(12) United States Patent
Brahm et al.

(10) Patent No.: US 10,537,110 B2
(45) Date of Patent: Jan. 21, 2020

(54) PESTICIDAL MIXTURES

(71) Applicant: BASF Corporation, Florham Park, NJ (US)

(72) Inventors: Lutz Brahm, Worms (DE); Burghard Liebmann, Bensheim (DE); Ronald Wilhelm, Hofheim (DE); Markus Gewehr, Kastellaun (DE)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 14/443,844

(22) PCT Filed: Nov. 12, 2013

(86) PCT No.: PCT/EP2013/073529
§ 371 (c)(1),
(2) Date: May 19, 2015

(87) PCT Pub. No.: WO2014/079719
PCT Pub. Date: May 30, 2014

(65) Prior Publication Data
US 2015/0296801 A1    Oct. 22, 2015

(30) Foreign Application Priority Data

Nov. 22, 2012  (EP) .................................... 12193738
Sep. 17, 2013  (EP) .................................... 13184836

(51) Int. Cl.
| | | |
|---|---|---|
| *A01N 63/04* | (2006.01) | |
| *A01N 25/00* | (2006.01) | |
| *A01N 37/42* | (2006.01) | |
| *A01N 43/56* | (2006.01) | |
| *A01N 53/00* | (2006.01) | |

(52) U.S. Cl.
CPC ............. *A01N 63/04* (2013.01); *A01N 25/00* (2013.01)

(58) Field of Classification Search
CPC combination set(s) only.
See application file for complete search history.

(56) References Cited

U.S. PATENT DOCUMENTS

| | | | |
|---|---|---|---|
| 5,631,276 A | 5/1997 | Kern | |
| 5,885,598 A | 3/1999 | Knauf et al. | |
| 8,445,255 B2 | 5/2013 | Kloepper et al. | |
| 2003/0068303 A1 | 4/2003 | Selvig et al. | |
| 2003/0224936 A1* | 12/2003 | Kretzschmar | ............ A01C 1/06 504/100 |
| 2007/0244073 A1* | 10/2007 | Angst | .................... A01N 43/56 514/86 |
| 2012/0076765 A1 | 3/2012 | Schisler et al. | |
| 2012/0094834 A1 | 4/2012 | Frank et al. | |
| 2012/0149571 A1 | 6/2012 | Kloepper et al. | |

FOREIGN PATENT DOCUMENTS

| | | |
|---|---|---|
| CN | 1086664 | 5/1994 |
| CN | 101028009 A | 9/2007 |
| CN | 101697736 A | 4/2010 |
| CN | 101697737 A | 4/2010 |
| GB | 2481118 A | 12/2011 |
| WO | WO 94/10846 A1 | 5/1994 |
| WO | WO 96/19112 A1 | 6/1996 |
| WO | WO 2009/037242 A2 | 3/2009 |
| WO | WO 2010/139656 A2 | 12/2010 |
| WO | WO 2011/117272 A2 | 9/2011 |
| WO | WO 2011/147953 A1 | 12/2011 |
| WO | WO 2012/072696 | 6/2012 |
| WO | WO 2012/076563 A1 | 6/2012 |
| WO | WO 2014/053398 A1 | 4/2014 |
| WO | WO 2014/079719 A1 | 5/2014 |
| WO | WO 2014/079724 | 5/2014 |
| WO | WO 2014/079728 A1 | 5/2014 |
| WO | WO 2014/079764 A1 | 5/2014 |
| WO | WO 2014/079766 A1 | 5/2014 |
| WO | WO 2014/079770 | 5/2014 |
| WO | WO 2014/079771 A1 | 5/2014 |
| WO | WO 2014/079772 | 5/2014 |
| WO | WO 2014/079773 A1 | 5/2014 |
| WO | WO 2014/079774 | 5/2014 |
| WO | WO 2014/079804 A1 | 5/2014 |
| WO | WO 2014/079814 A1 | 5/2014 |
| WO | WO 2014/079841 A1 | 5/2014 |

OTHER PUBLICATIONS

Echeveeri-Molina, D. et al., "Toxicity of synthetic and biological insecticides against adults of the Eucalyptus snout-beetle Gonipterus scutellatus Gyllenhal (Coleoptera: Curculionidae)," Journal of Pest Science, vol. 83, pp. 297-305 (2010).*

Singh, V. et al., "DuPont CyazypyrTM (DPX-HGW86, cyantraniliprole): a cross-spectrum insecticide for control of major pests of rice," abstract of conference paper, Entomological Society of America Annual, Nov. 2011; Retrieved from the Internet on Feb. 9, 2017: <https://www.researchgate.net/publication/267528306_DuPont_Cyazypyr_DPX-HGW86_c >.*

"Broadband", (Aug, 9, 2012), retrieved from Intnet Jan. 29, 2014 url: http://beckerunderwood.com/media/products/resources/broadband_instructions_B4D27D46613D6.pdf.

(Continued)

*Primary Examiner* — John Pak

(74) *Attorney, Agent, or Firm* — Brinks Gilson & Lione

(57) ABSTRACT

The present invention relates to pesticidal mixtures comprising one biological compound selected from the group consisting of *Beauveria bassiana* PPRI 5339, *Metarhizium anisopliae* FI-1045, *Metarhizium anisopliae* var. *acridum* FI-985 and *Metarhizium anisopliae* var. *acridum* IMI 330189 and one fungicidal or insecticidal or plant growth regulating compound and respective agricultural uses thereof.

7 Claims, No Drawings

(56) References Cited

OTHER PUBLICATIONS

Bennett, Amanda J., et al., "Survival of the biocontrol agents *Coniothyrium minitans* and *Bacillus subtilis* MBI 600 introduced into pasteurized, sterilized and non-sterile soils", *Soil Biology & Biochemistry*, 2003, vol. 35, pp. 1565-1573, UK.
International Search Report for PCT/EP2013/073529, dated Mar. 24, 2014.
Enebak, S.A, et al., "Evidence for Induced Systemic Protection to Fusiform Rust in Loblolly Pine by Plant Growth-Promoting Rhizobacteria", *The American Phytopathological Society*, Plant Disease/Mar. 2000, vol. 84, No. 3, pp. 306-308.
Farenhorst, M., et al., "Synergy in Efficacy of Fungal Entomopathogens and Permethrin against West African Insecticide-Resistant *Anopheles gambiae* Mosquitoes", *PLOS One*, vol. 5, No. 8 (Jan. 2010), pp. 1-10.
Koch, Thomas, et al., "Biosynthesis of cis-Jasmone: A Pathway for the Inactivation and the Disposal of the Plant Stress Hormone Jasmonic Acid to the Gas Phase?", *Helvetica Chimica Acta*, 1997, vol. 80, pp. 838-850, Switzerland.
Leisso, R. S., et al., "The influence of biological and fungicidal seed treatments on chickpea (*Cicer arietinum*) damping off", *Canadian Journal of Plant Pathology*, 2009, vol. 31, pp. 38-46, CA.
McKnight, S. E., et al., "Root Colonization of Cotton Seedlings by *Bacillus subtilis* (MBI 600)", $2^{nd}$ International Workshop on Plant Growth-Promoting Rhizobacteria,(1991), pp. 365-369.
Schmidt, C. S., et al., "Influence of Soil Temperature and Matric Potential on Sugar Beet Seedling Colonization and Suppression of Pythium Damping-Off by the Antagonistic Bacteria *Pseudomonas fluorescens* and *Bacillus subtilis*", *The American Phytopathological Society*, Phytopathology/2004, vol. 94, No. 4, pp. 351-363.
Unknown Author, "Broadband", Reg. No. L 8270 Act. No. 36 of 1947 by Becker Underwood BioAg SA (Pty) Ltd., date unknown, South Africa.
Wright, B., et al., "Application of Beneficial Microorganisms to Seeds during Drum Priming", *Biocontrol Science and Technology*, Sep. 2003, vol. 13, No. 6, pp. 599-614, UK.
Zhang, Shouan, et al., "Evaluation of Microbial Products for Management of Powdery Mildew on Summer Squash and Cantaloupe in Florida", *The American Phytopathological Society*, Plant Disease/Apr. 2011, vol. 95, No. 4, pp. 461-468.
Zhou, X. G., et al., "Field evaluation of a beneficial *Bacillus* strain for biocontrol of sheath blight in rice", *Phytopathology*, 2011, vol. 101, S204.
Office Action, issued in co-pending U.S. Appl. No. 14/443,520, dated Oct. 14, 2016.
Office Action, issued in co-pending U.S. Appl. No. 14/443,206, dated Apr. 5, 2017.
Office Action, issued in Chinese Application No. 201380071087.5, dated Apr. 26, 2017 (with translation).
Office Action, issued in Eurasian Application No. 201506049, dated Feb. 14, 2017 (with translation).
Farenhorst et al., "Synergy in Efficacy of Fungal Entomopathogens and Permethrin against West African Insecticide-Resistant *Anopheles gambiae* Mosquitoes," *PLoS ONE*, 2010, vol. 5, Issue 8, pp. 1-10.

\* cited by examiner

PESTICIDAL MIXTURES

DESCRIPTION

This application is a National Stage application of International Application No. PCT/EP2013/073529 filed Nov. 12, 2013, the entire contents of which is hereby incorporated herein by reference. This application also claims priority under 35 U.S.C. § 119 to European Patent Application No. 12193738.7, filed Nov. 22, 2012 and European Patent Application No. 13184836.8, filed Sep. 17, 2013, the entire contents of which is hereby incorporated herein by reference.

The present invention relates to synergistic mixtures comprising as active components,
1) one fungicidal compound A selected from the group consisting of
   A) Respiration inhibitors
      Inhibitors of complex III at Qo site: azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide, pyribencarb, triclopyricarb/chlorodincarb, famoxadone, fenamidone;
      inhibitors of complex III at Qi site: cyazofamid, amisulbrom, [(3S,6S,7R,8R)-8-beftnzyl-3-[(3-acetoxy-4-methoxy-pyridine-2-carbonyl)amino]-6-methyl-4,9-dioxo-1,5-dioxonan-7-yl]2-methyl-propanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol -5-ylmethoxy)-4-methoxy-pyridine-2-carbonyl]amino]-6-methyl-4,9-dioxo-1,5-dioxonan-7-yl]2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl2-methylpropanoate
      inhibitors of complex II: flutolanil, benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide (benzovindiflupyr), 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide;
      other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentinacetate, fentin chloride or fentin hydroxide; ametoctradin; and silthiofam;
   B) Sterol biosynthesis inhibitors (SBI fungicides)
      C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H-[1,2,4]triazole, 2-[rel-(2S;3R)-3-(2-chlorophenyl)-2-(2,4-difluorophenyl)-oxiranylmethyl]-2H-[1,2,4]triazole-3-thiol; imidazoles: imazalil, pefurazoate, prochloraz, triflumizol; pyrimidines, pyridines and piperazines: fenarimol, nuarimol, pyrifenox, triforine;
      Delta14-reductase inhibitors: aldimorph, dodemorph, dodemorph-acetate, fenpropimorph, tridemorph, fenpropidin, piperalin, spiroxamine;
      Inhibitors of 3-keto reductase: fenhexamid;
   C) Nucleic acid synthesis inhibitors
      phenylamides or acyl amino acid fungicides: benalaxyl, benalaxyl-M, kiral-axyl, metalaxyl, ofurace, oxadixyl;
      others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy)pyrimidin-4-amine;
   D) Inhibitors of cell division and cytoskeleton
      tubulin inhibitors: benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine
      other cell division inhibitors: diethofencarb, ethaboxam, pencycuron, fluopicolide, zoxamide, metrafenone, pyriofenone;
   E) Inhibitors of amino acid and protein synthesis
      methionine synthesis inhibitors (anilino-pyrimidines): cyprodinil, mepanipyrim, pyrimethanil;
      protein synthesis inhibitors: blasticidin-S, kasugamycin, kasugamycin hydrochloride-hydrate, mildiomycin, streptomycin, oxytetracyclin, polyoxine, validamycin A;
   F) Signal transduction inhibitors
      MAP/histidine kinase inhibitors: fluoroimid, iprodione, procymidone, vinclozolin, fenpiclonil, fludioxonil;
      G protein inhibitors: quinoxyfen;

G) Lipid and membrane synthesis inhibitors
Phospholipid biosynthesis inhibitors: edifenphos, iprobenfos, pyrazophos, isoprothiolane;
lipid peroxidation: dicloran, quintozene, tecnazene, tolclofos-methyl, biphenyl, chloroneb, etridiazole;
phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl)carbamic acid-(4-fluorophenyl)ester;
compounds affecting cell membrane permeability and fatty acides: propamocarb, propamocarb-hydrochlorid
fatty acid amide hydrolase inhibitors: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone H) Inhibitors with Multi Site Action
inorganic active substances: Bordeaux mixture, copper acetate, copper hydroxide, copper oxychloride, basic copper sulfate, sulfur;
thio- and dithiocarbamates: ferbam, mancozeb, maneb, metam, metiram, propineb, thiram, zineb, ziram;
organochlorine compounds (e.g. phthalimides, sulfamides, chloronitriles): anilazine, chlorothalonil, captafol, captan, folpet, dichlofluanid, dichlorophen, hexachlorobenzene, pentachlorphenole and its salts, phthalide, tolylfluanid, N-(4-chloro-2-nitro-phenyl)-N-ethyl-4-methylbenzenesulfonamide;
guanidines and others: guanidine, dodine, dodine free base, guazatine, guazatine-acetate, iminoctadine, iminoctadine-triacetate, iminoctadinetris(albesilate), dithianon, 2,6-dimethyl-1H,5H-[1,4]dithiino[2,3-c:5,6-c']dipyrrole-1,3,5,7(2H,6H)-tetraone;

I) Cell wall synthesis inhibitors
Inhibitors of glucan synthesis: validamycin, polyoxin B; melanin synthesis inhibitors: pyroquilon, tricyclazole, carpropamid, dicyclomet, fenoxanil;

J) Plant defence inducers
acibenzolar-S-methyl, probenazole, isotianil, tiadinil, prohexadione-calcium; 4-cyclopropyl-N-(2,4-dimethoxyphenyl)thiadiazole-5-carboxamide; phosphonates: fosetyl, fosetyl-aluminum, phosphorous acid and its salts;

K) Unknown mode of action
bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxine-copper, picarbutrazox, proquinazid, tebufloquin, tecloftalam, triazoxide, 2-butoxy-6-iodo-3-propylchromen-4-one, N-(cyclopropylmethoxy-imino-(6-difluoro-methoxy-2,3-difluoro-phenyl)-methyl)-2-phenyl acetamide, N'-(4-(4-chloro-3-trifluoromethyl-phenoxy)-2,5-dimethylphenyl)-N-ethyl-N-methyl formamidine, N'-(4-(4-fluoro-3-trifluoromethylphenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chloro-phenyl)-2,3-dimethyl-isoxazolidin-3-yl]-pyridine (pyrisoxazole), N-(6-methoxy-pyridin-3-yl)cyclopropanecarboxylic acid amide, 5-chloro-1-(4,6-dimethoxy-pyrimidin-2-yl)-2-methyl-1H-benzoimidazole, 2-(4-chlorophenyl)-N-[4-(3,4-dimethoxy-phenyl)-isoxazol-5-yl]-2-prop-2-ynyloxy-acetamide, 4,4-difluoro-3,3-dimethyl-1-(3-quinolyl)isoquinoline;

L) Antifungal biological Control Agents:
Ampelomyces quisqualis (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amyloliquefaciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), Fusarium oxysporum (e.g. BIOFOX® from S.I.A.P.A., Italy, FUSACLEAN® from Natural Plant Protection, France), *Metschnikowia fructicola* (e.g. SHEMER® from Agrogreen, Israel), Microdochium dimerum (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone Bio-Innovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICO- VAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ); or 2) one insecticidal compound IB selected from the group consisting of

- M-1.A acetylcholine esterase inhibitors from the class of carbamates: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, and triazamate;
- M-1.B acetylcholine esterase inhibitors from the class of organophosphates: acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;
- M-2 GABA-gated chloride channel antagonists:
- M-2.A cyclodiene organochlorine compounds: endosulfan; or
- M-2.B fiproles (phenylpyrazoles): ethiprole, fipronil, flufiprole, pyrafluprole, or pyriprole;
- M-2. Others: 4-[5-[3-chloro-5-(trifluoromethyl)phenyl]-5-(trifluoromethyl)-4H-isoxazol-3-yl]-N-[2-oxo-2-(2,2,2-trifluoroethylamino)ethyl]naphthalene-1-carboxamide, 4-[5-(3,5-dichlorophenyl)-5-(trifluoromethyl)-4H-isoxazol-3-yl]-2-methyl-N-[2-oxo-2-(2,2,2-trifluoroethylamino)ethyl]benzamide;
- M-3 sodium channel modulators from the class of pyrethroids: acrinathrin, allethrin, d-cis-trans allethrin, d-trans allethrin, bifenthrin, bioallethrin, bioallethrin S-cylclopentenyl, bioresmethrin, cycloprothrin, cyfluthrin, betacyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, momfluorothrin, empenthrin, esfenvalerate, etofenprox, fenpropathrin, fenvalerate, flucythrinate, flumethrin, tau-fluvalinate, halfenprox, imiprothrin, meperfluthrin,metofluthrin, permethrin, phenothrin, prallethrin, profluthrin, pyrethrin (pyrethrum), resmethrin, silafluofen, tefluthrin, tetramethylfluthrin, tetramethrin, tralomethrin, transfluthrin, DDT and methoxychlor;
- M-4 nicotinic aceylcholine receptor agonists from the class of neonicotinoids: acteamiprid, chlothianidin, cycloxaprid, dinotefuran, flupyradifurone, imidacloprid, nitenpyram, sulfoxaflor, thiacloprid, thiamethoxam, 1-[(6-chloro-3-pyridyl)methyl]-7-methyl-8-nitro-5-propoxy-3,5,6,7-tetrahydro-2H-imidazo[1,2-a]pyridine or 1-[(6-chloro-3-pyridyl)methyl]-2-nitro-1-[(E)-pentylideneamino]guanidine;
- M-5 allosteric nicotinic aceylcholine receptor activators from the class of spinosyns: spinosad, spinetoram;
- M-6 chloride channel activators from the class of mectins: abamectin, emamectin benzoate, ivermectin, lepimectin or milbemectin;
- M-7 juvenile hormone mimics: hydroprene, kinoprene, methoprene, fenoxycarb or pyriproxyfen;
- M-8 non-specific multi-site inhibitors: methyl bromide and other alkyl halides, chloropicrin, sulfuryl fluoride, borax or tartar emetic;
- M-9 selective homopteran feeding blockers: pymetrozine, flonicamid, pyrifluquinazon, 2-(5-fluoro-3-pyridyI)-5-(6-pyrimidin-2-yl-2-pyridyl)thiazole hydrofluoride
- M-10 mite growth inhibitors: clofentezine, hexythiazox, diflovidazin or etoxazole;
- M-11 inhibitors of mitochondrial ATP synthase: diafenthiuron, azocyclotin, cyhexatin, fenbutatin oxide, propargite, or tetradifon;
- M-12 uncouplers of oxidative phosphorylation: chlorfenapyr, DNOC, or sulfluramid;
- M-13 nicotinic acetylcholine receptor channel blockers: bensultap, cartap hydrochloride, thiocyclam, thiosultap sodium;
- M-14 inhibitors of the chitin biosynthesis type 0 (benzoylurea class): bistrifluron, chlorfluazuron, diflubenzuron, flucycloxuron, flufenoxuron, hexaflumuron, lufenuron, novaluron, noviflumuron, teflubenzuron, triflumuron;
- M-15 inhibitors of the chitin biosynthesis type 1: buprofezin;
- M-16 moulting disruptors: cyromazine;
- M-17 Ecdyson receptor agonists: methoxyfenozide, tebufenozide, halofenozide, fufenozide or chromafenozide;
- M-18 Octopamin receptor agonists: amitraz;
- M-19 Mitochondrial complex III electron transport inhibitors: hydramethylnon, acequinocyl, flometoquin, fluacrypyrim or pyriminostrobin;
- M-20 Mitochondrial complex I electron transport inhibitors: fenazaquin, fenpyroximate, pyrimidifen, pyridaben, tebufenpyrad, tolfenpyrad, flufenerim, or rotenone;
- M-21 Voltage-dependent sodium channel blockers: indoxacarb, metaflumizone or 1-[(E)42-(4-cyanophenyl)-1-[3-(trifluoromethyl)phenyl]ethylidene]-amino]-3-[4-(difluoromethoxy)phenyl]urea;
- M-22 Inhibitors of the lipid synthesis, inhibitors of acetyl CoA carboxylase: spirodiclofen, spiromesifen or spirotetramat;
- M-23 Mitochondrial complex II electron transport inhibitors: cyenopyrafen, cyflumetofen or pyflubumide; and
- M-24 Ryanodine receptor-modulators from the class of diamides: flubendiamide, chloranthraniliprole (rynaxypyr), cyanthraniliprole (cyazypyr), (R)-3-chloro-N1-{2-methyl-4-[1,2,2,2-tetrafluoro-1-(trifluoromethyl)ethyl]phenyl}-N2-(1-methyl-2-methylsulfonylethyl)phthalamide, (S)-3-chloro-N1-{2-methyl-4-[1,2,2,2-tetrafluoro-1-(trifluormethyl)ethyl]phenyl}-N2-(1-methyl-2-methylsulfonylethyl)phthalamide, 3-bromo-N-{2-bromo-4-chloro-6-[(1-cyclopropylethyl)carbamoyl]phenyl}-1-(3-chloropyridin-2-yl)-1H-pyrazole-5-carboxamide, methyl-2-8 3,5-dibromo-2-({[3-bromo-1-(3-chloro-pyridin-2-yl)-1H-pyrazol-5-yl]carbonyl}amino)ben-zoyl]-1,2-dimethylhydrazinecarboxylate (known from WO 2007/043677), N2-[2-(3-chloro-2-pyridyl)-5-[(5-methyltetrazol-2-yl)methyl]pyrazol-3-yl]-5-cyano-N1,3-dimethylphthalamide, N2-(1-cyano-1-methyl-ethyl)-N1-(2,4-dimethylphenyl)-3-iodophthalamide, 3-chloro-N2-(1-cyano-1-methyl-ethyl)-N1-(2,4-dimethylphenyl), 2-(3-chloro-2-pyridyl)-N-[4-cyano-2-methyl-6-(methylcarbamoyl)phenyl]-5-[5-(trifluoromethyl)tetrazol-2-yl]methyl]pyrazole-3-carboxamide, N-[2-(tert-butylcarbamoyl)-4-chloro-6-methyl-phenyl]-2-(3-chloro-2-pyridyl)-5-(fluoromethoxy)pyrazole-3-carboxamide, 5-bromo-N-[2,4-dichloro-6-(methylcarbamoyl)phenyl]-2-(3,5-dichloro-2-pyridyl)pyrazole-3-carboxamide, 5-chloro-2-(3-chloro-2-pyridyl)-N-[2,4-dichloro-6-[(1-cyano-1-methyl-ethyl)carbamoyl]phenyl]pyrazole-3-carboxamide, N-[2-(5-amino-1,3,4-thiadiazol-2-yl)-4-chloro-6-methyl-phenyl]-5-bromo-2-(3-chloro-2-pyridyl)pyrazole-3-carboxamide;

M-25 Others: afidopyropen, 2-(5-ethylsulfinyl-2-fluoro-4-methyl-phenyl)-5-methyl-1,2,4-triazol-3-amine, 1-(5-ethylsulfinyl-2,4-dimethyl-phenyl)-3-methyl-1,2,4-triazole, triflumezopyrim, 8-chloro-N-[2-chloro-5-methoxyphenyl)sulfonyl]-6-trifluoromethyl)-imidazo[1,2-a]pyridine-2-carboxamide, 5-[3-[2,6-dichloro-4-(3,3-dichloroallyloxy)phenoxy]propoxy]-1H-pyrazole, N-[1-[(6-chloro-3-pyridyl)methyl]-2-pyridylidene]-2,2,2-trifluoro-acetamide, N-[1-[(6-chloro-3-pyridyl)methyl]-2-pyridylidene]-2,2,3,3,3-penta-fluoro-propanamide, N-[1-[(6-bromo-3-pyridyl)methyl]-2-pyridylidene]-2,2,2-trifluoro-acetamide, N-[1-[(2-chloropyrimidin-5-yl)methyl]-2-pyridylidene]-2,2,2-trifluoro-acetamide, N-[1-[(6-chloro-5-fluoro-3-pyridyl)methyl]-2-pyridylidene]-2,2,2-trifluoro-acetamide, 2,2,2-trifluoro-N-[1-[(6-fluoro-3-pyridyl)methyl]-2-pyridylidene]acetamide, 2-chloro-N41-[(6-chloro-3-pyridyl)methyl]-2-pyridylidene]-2,2-difluoro-acetamide, N-[1-[1-[(6-chloro-3-pyridyl)ethyl]-2-pyridylidene]-2,2,2-trif-luoro-acetamide, N-[1-[(6-chloro-3-pyridyl)methyl]-2-pyridylidene]-2,2-difluoro-acetamide; 11-(4-chloro-2,6-dimethylphenyl)-12-hydroxy-1,4-dioxa-9-azadispiro[4.2.4.2]-tetradec-11-en-10-one, 3-(4'-fluoro-2,4-dimethylbiphenyl-3-yl)-4-hydroxy-8-oxa-1-azaspiro[4.5]dec-3-en-2-one, 2-(5-fluoro-3-pyridyl)-5-(6-pyrimidin-2-yl-2-pyridyl)thiazole hydrofluoride, 2-(3-pyridyl)-5-(6-pyrimidin-2-yl-2-pyridyl)thiazole, 5-[6-(1,3-dioxan-2-yl)-2-pyridyl]-2-(3-pyridyl)thiazole, 4-[5-[3-chloro-5-(trifluorom-ethyl)phenyl]-5-(trifluoromethyl)-4H-isoxazol-3-yl]-N-[2-oxo-2-(2,2,2-trifluoroethylamino)ethyl]naphthalene-1-carboxamide, 4-[5-(3,5-dichlorophenyl)-5-(trifluoromethyl)-4H-isoxazol-3-yl]-2-methyl-N-[2-oxo-2-(2,2,2-trifluoroethylamino)ethyl]benzamide, 4-[5-(3,5-dichloro-phenyl)-5-(trifluoromethyl)-4H-isoxazol-3-yl]-2-methyl-N-(1-oxothietan-3-yl)-benzamide, methaldehyde;

M-26: *Bacillus firmus* (e.g. *Bacillus firmus* CNCM 1-1582, e.g. WO09126473A1 and WO09124707 A2, commercially available as "Votivo")

or 3) one compound IC having plant growth regulator activity selected from the group consisting of:

Antiauxins: clofibric acid, 2,3,5-tri-iodobenzoic acid;

Auxins: 4-CPA, 2,4-D, 2,4-DB, 2,4-DEP, dichlorprop, fenoprop, IAA (indole-3-acetic acid), IBA, naphtha-leneacetamide, α-naphthaleneacetic acid, 1-naph-thol, naphthoxyacetic acid, potassium naphthenate, sodium naphthenate, 2,4,5-T;

Cytokinins: 2iP, 6-benzylaminopurine (6-BA) (=N-6-benzyladenine), 2,6-dimethylpuridine (N-Oxide-2,6-lultidine), 2,6-dimethylpyridine, kinetin, zeatin;

Defoliants: calcium cyanamide, dimethipin, endothal, merphos, metoxuron, pentachlorophenol, thidiaz-uron, tribufos, tributyl phosphorotrithioate;

Ethylene modulators: aviglycine, 1-methylcyclopro-pene (1-MCP), prohexadione (prohexadione cal-cium), trinexapac (trinexapac-ethyl);

Ethylene releasers: ACC, etacelasil, ethephon, glyox-ime;

Gibberellins: gibberelline, gibberellic acid;

Growth inhibitors: abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepi-quat (mepiquat chloride, mepiquat pentaborate), piproctanyl, prohydrojasmon, propham, 2,3,5-tri-io-dobenzoic acid;

Morphactins: chlorfluren, chlorflurenol, dichlorflure-nol, flurenol;

Growth retardants: chlormequat (chlormequat chlo-ride), daminozide, flurprimidol, mefluidide, paclobutrazol, tetcyclacis, uniconazole, metcon-azole;

Growth stimulators: brassinolide, forchlorfenuron, hymexazol;

Unclassified plant growth regulators/classification unknown: amidochlor, benzofluor, buminafos, car-vone, choline chloride, ciobutide, clofencet, cloxy-fonac, cyanamide, cyclanilide, cycloheximide, cyprosulfamide, epocholeone, ethychlozate, ethyl-ene, fenridazon, fluprimidol, fluthiacet, heptopargil, holosulf, inabenfide, karetazan, lead arsenate, metha-sulfocarb, pydanon, sintofen, triapenthenol; and 4) one compound II selected from the group consisting of *Beauveria bassiana* PPRI 5339, *Metarhizium anisopliae* FI-1045, *Metarhizium anisopliae* var. *acridum* FI-985, and *Metarhizium anisopliae* var. *acridum* IMI 330189.

The above-referred mixtures and all further embodiments of mixtures described herein below are for the purpose of this application also referred to as "inventive mixtures".

*Beauveria bassiana* PPRI 5339 has been deposited under ARSEF number 5339 in the USDA ARS collection of entomopathogenic fungal cultures (ARSEF=Agricultural Research Service Collection of Entomopathogenic Fungi) and is commercially available from Becker Underwood as product "BroadBand". It was also deposited at the "Agricultural Research Culture Collection" (NRRL) deposit number 50757 located in 1815 N. University Street; Peoria; Ill. 61604; U.S.A.

*Metarhizium anisopliae* FI-1045 has been deposited under ARSEF number 10469 in the USDA ARS collection of entomopathogenic fungal cultures and is commercially available from Becker Underwood as product "BioCane". BioCane™ granules are registered for the control of greyback canegrub (i.e. Dermolepida albohirtum) in Australian sugarcane fields.

*Metarhizium anisopliae* var. *acridum* FI-985 has been deposited under ARSEF number 7970 in the USDA ARS collection of entomopathogenic fungal cultures and is commercially available from Becker Underwood as product "GreenGuard". Information on FI-985 can be found for example in "Review of the efficacy of *Metarhizium anisopliae* var. *acridum* against the Desert Locust" (FAO; Plant Production and Protection Division; 2007) as well as in Magalhães et al., 2003 "Characterization of a Peruvian isolate of *Metarhizium anisopliae* var. *acridum*, a pathogen of grasshoppers" or Richard J. Milner; Memoirs of the Entomological Society of Canada/Volume 129/Supplement S171/January 1997, pp 287-300: "*METARHIZIUM FLAVO-VIRIDE* (FI-985) AS A PROMISING MYCOINSECTICIDE FOR AUSTRALIAN ACRIDIDS".

*Metarhizium anisopliae* var. *acridum* IMI 330189 has been deposited at the European Culture Collections CABI, Bakeham Lane, Egham, Surrey, TW20 9TY, United Kingdom, and is commercially available from Becker Underwood as product "Green Muscle". It was also deposited at the "Agricultural Research Culture Collection" (NRRL) deposit number 50758 located in 1815 N. University Street; Peoria; Ill. 61604; U.S.A. Information on IMI 330189 can be found in Lomer et al.; Agricultural and Forest Entomology (1999) 1, 71-88: "Development of strategies for the incorporation of biological pesticides into the integrated management of locusts and grasshoppers".

*Metarhizium anisopliae* var. *acridum* is nowadys called *Metarhizium acridum* (Synonym).

Thus, the present invention relates to synergistic mixtures comprising *Beauveria bassiana* PPRI 5339 and one compound IA.

The present invention furthermore relates to synergistic mixtures comprising *Metarhizium anisopliae* FI-1045 and one compound IA.

The present invention furthermore relates to synergistic mixtures comprising *Metarhizium anisopliae* var. *acridum* FI-985 and one compound IA.

The present invention furthermore relates to synergistic mixtures comprising *Metarhizium anisopliae* var. *acridum* IMI 330189 and one compound IA.

Thus, the present invention relates to synergistic mixtures comprising *Beauveria bassiana* PPRI 5339 and one compound IB.

The present invention furthermore relates to synergistic mixtures comprising *Metarhizium anisopliae* FI-1045 and one compound IB.

The present invention furthermore relates to synergistic mixtures comprising *Metarhizium anisopliae* var. *acridum* FI-985 and one compound IB.

The present invention furthermore relates to synergistic mixtures comprising *Metarhizium anisopliae* var. *acridum* IMI 330189 and one compound IB.

Thus, the present invention relates to synergistic mixtures comprising *Beauveria bassiana* PPRI 5339 and one compound IC.

The present invention furthermore relates to synergistic mixtures comprising *Metarhizium anisopliae* FI-1045 and one compound IC.

The present invention furthermore relates to synergistic mixtures comprising *Metarhizium anisopliae* var. *acridum* FI-985 and one compound IC.

The present invention furthermore relates to synergistic mixtures comprising *Metarhizium anisopliae* var. *acridum* IMI 330189 and one compound IC.

The compounds IA, IB and IC and methods for producing them are generally known. For instance, they may be found in the e-Pesticide Manual V5.2 (ISBN 978 1 901396 85 0) (2008-2011) among other publications or in the references given above.

In R. J. Milner, P. R. Samson, G. K. Bullard in Biocontrol Science and Technology 01/2002; 12(1): 43-58. (Published online: 28 Jun. 2010) "FI-1045: A Profile of a Commercially Useful Isolate of *Metarhizium anisopliae* var. anisopliae" *Metarhizium anisopliae* FI-1045 is described in detail.

One typical problem arising in the field of pest control lies in the need to reduce the dosage rates of the active ingredient in order to reduce or avoid unfavorable environmental or toxicological effects whilst still allowing effective pest control.

In regard to the instant invention the term pests embrace animal pests, and harmful fungi.

Another problem encountered concerns the need to have available pest control agents which are effective against a broad spectrum of pests, e.g. both animal pests and harmful fungi.

There also exists the need for pest control agents that combine knock-down activity with prolonged control, that is, fast action with long lasting action.

Another difficulty in relation to the use of pesticides is that the repeated and exclusive application of an individual pesticidal compound leads in many cases to a rapid selection of pests, that means animal pests, and harmful fungi, which have developed natural or adapted resistance against the active compound in question. Therefore there is a need for pest control agents that help prevent or overcome resistance.

Another problem underlying the present invention is the desire for compositions that improve plants, a process which is commonly and hereinafter referred to as "plant health".

It was therefore an object of the present invention to provide pesticidal mixtures which solve the problems of reducing the dosage rate and/or enhancing the spectrum of activity and/or combining knock-down activity with prolonged control and/or to resistance management and/or promoting (increasing) the health of plants.

We have found that this object is in part or in whole achieved by the mixtures comprising the active compounds defined in the outset.

In particular, it has been found that the action of the inventive mixtures goes far beyond the fungicidal and/or insecticidal and/or plant health improving action of the active compounds I and II present in the mixture alone (synergism).

As used herein, the term "insecticidal" (or "insect attack") also denotes not only action against (or attack by) insects, but also against (by) arachnids and nematodes.

Herein, we have found that simultaneous, that is joint or separate, application of the compound I and the compound II or successive application of the compound I and the compound II allows enhanced control of pests, that means harmful fungi or animal pests, compared to the control rates that are possible with the individual compounds (synergistic mixtures). Thus, the present invention relates to the inventive mixtures having synergistically enhanced action of controlling harmful fungi. Moreover, the invention relates to a method for controlling pest, using the inventive mixtures having synergistically enhanced action for controlling pests and to the use of compound I and compound II for preparing such mixtures, and also to compositions comprising such mixtures, wherein such methods relate seed treatment or foliar application or soil application.

Herein, we have found that simultaneous, that is joint or separate, application of the compound I and the compound II or successive application of the compound I and compound II provides enhanced plant health effects compared to the plant health effects that are possible with the individual compounds (synergistic mixtures). Thus, the present invention relates to inventive mixtures having synergistically enhanced action of increasing the health of plants. Moreover, the invention relates to a method for improving the health of plants, using the inventive mixtures having synergistically enhanced action for improving the health of plants and to the use of compound I and compound II for preparing such mixtures, and also to compositions comprising such mixtures, wherein such methods relate seed treatment or foliar application or soil application.

In particular, the present invention relates to a method for controlling pests and/or improving the health of plants, wherein the pest, their habitat, breeding grounds, their locus or the plants to be protected against pest attack are treated with an effective amount of an inventive mixture.

In a preferred embodiment, the present invention relates to a method for controlling pests, wherein the pest, their habitat, breeding grounds, their locus or the plants to be protected against pest attack are treated with an effective amount of an inventive mixture.

In an equally preferred embodiment, the present invention relates to a method for controlling harmful fungi, wherein the fungi, their habitat, breeding grounds, their locus or the plants to be protected against fungal attack are treated with an effective amount of an inventive mixture comprising compound IA and compound II.

In an equally preferred embodiment, the present invention relates to a method for controlling animal pests (insects, acarids or nematodes), wherein the animal pests (insects, acarids or nematodes), their habitat, breeding grounds, their locus or the plants to be protected against animal pest (insects, acarids or nematodes) attack are treated with an effective amount of an inventive mixture comprising compound IB and compound II.

In an equally preferred embodiment, the present invention relates to a method for regulating plant growth, wherein the plants are treated with an effective amount of an inventive mixture comprising compound IC and compound II.

In an equally preferred embodiment, the present invention relates to a method for improving the health of plants, wherein the plants are treated with an effective amount of an inventive mixture.

In particular, the present invention relates to a method for protection of plant propagation material from pests and/or improving the health of plants, wherein the plant propagation material is treated with an effective amount of an inventive mixture.

In particular, the present invention relates to a method for protection of plant propagation material from pests, wherein the plant propagation material is treated with an effective amount of an inventive mixture.

In a preferred embodiment, the present invention relates to a method for protection of plant propagation material from animal pests (insects, acarids or nematodes), wherein the plant propagation material are treated with an effective amount of an inventive mixture.

In an equally preferred embodiment, the present invention relates to a method for protection of plant propagation material from harmful fungi, wherein the plant propagation material is treated with an effective amount of an inventive mixture.

In an equally preferred embodiment, the present invention relates to a method for improving the health of plants grown from said plant propagation material, wherein the plant propagation material is treated with an effective amount of an inventive mixture.

In particular, the present invention relates to a method for protection of plant propagation material from pests and/or improving the health of plants grown from said plant propagation material, wherein the soil, wherein plant propagation material is sown, is treated with an effective amount of an inventive mixture.

In particular, the present invention relates to a method for protection of plant propagation material from pests, wherein the soil, wherein plant propagation material is sown, is treated with an effective amount of an inventive mixture.

In particular, the present invention relates to a method for protection of plant propagation material from harmful fungi, wherein the soil, wherein plant propagation material is sown, is treated with an effective amount of an inventive mixture.

In particular, the present invention relates to a method for protection of plant propagation material from animal pests (insects, acarids or nematodes), wherein the soil, wherein plant propagation material is sown, is treated with an effective amount of an inventive mixture.

In particular, the present invention relates to a method for improving the health of plants grown from plant propagation material, wherein the soil, wherein plant propagation material is sown, is treated with an effective amount of an inventive mixture.

In all methods as described above, the compounds of the inventive mixtures can be applied simultaneously, that is jointly or separately, or in succession.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring. In a particular preferred embodiment, the term propagation material denotes seeds.

In general, "pesticidally effective amount" means the amount of the inventive mixtures or of compositions comprising the mixtures needed to achieve an observable effect on growth, including the effects of necrosis, death, retardation, prevention, and removal, destruction, or otherwise diminishing the occurrence and activity of the target organism. The pesticidally effective amount can vary for the various mixtures/compositions used in the invention. A pesticidally effective amount of the mixtures/compositions will also vary according to the prevailing conditions such as desired pesticidal effect and duration, weather, target species, locus, mode of application, and the like.

The term "plant health effective amount" denotes an amount of the inventive mixtures, which is sufficient for achieving plant health effects as defined herein below. More exemplary information about amounts, ways of application and suitable ratios to be used is given below. Anyway, the skilled artisan is well aware of the fact that such an amount can vary in a broad range and is dependent on various factors, e.g. the treated cultivated plant or material and the climatic conditions.

Healthier plants are desirable since they result among others in better yields and/or a better quality of the plants or crops, specifically better quality of the harvested plant parts. Healthier plants also better resist to biotic and/or abiotic stress. A high resistance against biotic stresses in turn allows the person skilled in the art to reduce the quantity of pesticides applied and consequently to slow down the development of resistances against the respective pesticides.

It was therefore an object of the present invention to provide a pesticidal composition which solves the problems outlined above, and which should, in particular, improve the health of plants, in particular the yield of plants.

The term "health of a plant" or "plant health" is defined as a condition of the plant and/or its products which is determined by several aspects alone or in combination with each other such as increased yield, plant vigor, quality of harvested plant parts and tolerance to abiotic and/or biotic stress.

It has to be emphasized that the above mentioned effects of the inventive mixtures, i.e. enhanced health of the plant, are also present when the plant is not under biotic stress and in particular when the plant is not under pest pressure.

For example, for foliar applications, it is evident that a plant suffering from fungal or insecticidal attack produces a smaller biomass and leads to a reduced yield as compared to a plant which has been subjected to curative or preventive treatment against the pathogenic fungus or any other relevant pest and which can grow without the damage caused by the biotic stress factor. However, the methods according to the invention lead to an enhanced plant health even in the absence of any biotic stress. This means that the positive effects of the mixtures of the invention cannot be explained just by the pesticidal activities of the compounds (I) and (II), but are based on further activity profiles. Accordingly, the application of the inventive mixtures can also be carried out in the absence of pest pressure.

For example, for seed treatment and soil applications, it is evident that a plant suffering from fungal or insecticidal attack shows reduced germination and emergence leading to poorer plant or crop establishment and vigor, and consequently, to a reduced yield as compared to a plant propagation material which has been subjected to curative or preventive treatment against the relevant pest and which can grow without the damage caused by the biotic stress factor. However, the methods according to the invention lead to an enhanced plant health even in the absence of any biotic stress. This means that the positive effects of the mixtures of the invention cannot be explained just by the pesticidal activities of the compounds (I) and (II), but are based on further activity profiles. Accordingly, the application of the inventive mixtures can also be carried out in the absence of pest pressure.

Each plant health indicator listed below, which is selected from the groups consisting of yield, plant vigor, quality and tolerance of the plant to abiotic and/or biotic stress, is to be understood as a preferred embodiment of the present invention either each on its own or preferably in combination with each other.

According to the present invention, "increased yield" of a plant means that the yield of a product of the respective plant is increased by a measurable amount over the yield of the same product of the plant produced under the same conditions, but without the application of the inventive mixture.

For foliar application forms, increased yield can be characterized, among others, by the following improved properties of the plant: increased plant weight; and/or increased plant height; and/or increased biomass such as higher overall fresh weight (FW); and/or increased number of flowers per plant; and/or higher grain and/or fruit yield; and/or more tillers or side shoots (branches); and/or larger leaves; and/or increased shoot growth; and/or increased protein content; and/or increased oil content; and/or increased starch content; and/or increased pigment content; and/or increased chlorophyll content (chlorophyll content has a positive correlation with the plant's photosynthesis rate and accordingly, the higher the chlorophyll content the higher the yield of a plant) and/or increased quality of a plant.

For seed treatment and soil application forms, increased yield can be characterized, among others, by the following improved properties of the plant:

increased plant weight; and/or increased plant height; and/or increased biomass such as higher overall fresh weight (FW); and/or increased number of flowers per plant; and/or higher grain and/or fruit yield; and/or more tillers or side shoots (branches); and/or larger leaves; and/or increased shoot growth; and/or increased protein content; and/or increased oil content; and/or increased starch content; and/or increased pigment content; and/or increased chlorophyll content (chlorophyll content has a positive correlation with the plant's photosynthesis rate and accordingly, the higher the chlorophyll content the higher the yield of a plant), increased quality of a plant.

"Grain" and "fruit" are to be understood as any plant product which is further utilized after harvesting, e.g. fruits in the proper sense, vegetables, nuts, grains, seeds, wood (e.g. in the case of silviculture plants), flowers (e.g. in the case of gardening plants, ornamentals) etc., that is anything of economic value that is produced by the plant.

According to the present invention, the yield is increased by at least 4%. In general, the yield increase may even be higher, for example 5 to 10%, more preferable by 10 to 20%, or even 20 to 30%

According to the present invention, the yield—if measured in the absence of pest pressure—is increased by at least 2% In general, the yield increase may even be higher, for example until 4% to 5% or even more.

Another indicator for the condition of the plant is the plant vigor. The plant vigor becomes manifest in several aspects such as the general visual appearance.

For foliar applications, improved plant vigor can be characterized, among others, by the following improved properties of the plant: improved vitality of the plant; and/or improved plant growth; and/or improved plant development; and/or improved visual appearance; and/or improved plant stand (less plant verse/lodging-and/or bigger leaf blade; and/or bigger size; and/or increased plant height; and/or increased tiller number; and/or increased number of side shoots; and/or increased number of flowers per plant; and/or increased shoot growth; and/or enhanced photosynthetic activity (e.g. based on increased stomatal conductance and/or increased $CO_2$ assimilation rate); and/or earlier flowering; and/or earlier fruiting; and/or earlier grain maturity; and/or less nonproductive tillers; and/or less dead basal leaves; and/or less input needed (such as fertilizers or water); and/or greener leaves; and/or complete maturation under shortened vegetation periods; and/or easier harvesting; and/or faster and more uniform ripening; and/or longer shelf-life; and/or longer panicles; and/or delay of senescence; and/or stronger and/or more productive tillers; and/or better extractability of ingredients; and/or improved quality of seeds (for being seeded in the following seasons for seed production); and/or reduced production of ethylene and/or the inhibition of its reception by the plant.

For seed treatment or soil applications, improved plant vigor can be characterized, among others, by the following improved properties of the plant: improved vitality of the plant; and/or improved plant growth; and/or improved plant development; and/or improved visual appearance; and/or improved plant stand (less plant verse/lodging); and/or improved emergence; and/or enhanced root growth and/or more developed root system; and/or enhanced nodulation, in particular rhizobial nodulation;and/or increased plant height; and/or increased tiller number; and/or increased number of side shoots; and/or increased number of flowers per plant; and/or increased shoot growth; and/or less non-productive tillersand/or less input needed (such as fertilizers or water); and/or less seeds needed; and/or stronger and/or more productive tillersand/or improved quality of seeds (for being seeded in the following seasons for seed production); and/or field establishment.

Another indicator for the condition of the plant is the "quality" of a plant and/or its products. According to the present invention, enhanced quality means that certain plant characteristics such as the content or composition of certain ingredients are increased or improved by a measurable or noticeable amount over the same factor of the plant produced under the same conditions, but without the application of the mixtures of the present invention. Enhanced quality can be characterized, among others, by following improved properties of the plant or its product: increased nutrient content; and/or increased protein content; and/or increased oil content; and/or increased starch content; and/or increased content of fatty acids; and/or increased metabolite content; and/or increased carotenoid content; and/or increased sugar content; and/or increased amount of essential amino acids; and/or improved nutrient composition; and/or improved protein composition; and/or improved composition of fatty acids; and/or improved metabolite composition; and/or improved carotenoid composition; and/or improved sugar composition; and/or improved amino acids composition; and/or improved or optimal fruit color; and/or improved leaf color; and/or higher storage capacity; and/or better processability of the harvested products.

Another indicator for the condition of the plant is the plant's tolerance or resistance to biotic and/or abiotic stress factors. Biotic and abiotic stress, especially over longer terms, can have harmful effects on plants.

Biotic stress is caused by living organisms while abiotic stress is caused for example by environmental extremes. According to the present invention, "enhanced tolerance or resistance to biotic and/or abiotic stress factors" means (1.) that certain negative factors caused by biotic and/or abiotic stress are diminished in a measurable or noticeable amount as compared to plants exposed to the same conditions, but without being treated with an inventive mixture and (2.) that the negative effects are not diminished by a direct action of the inventive mixture on the stress factors, e.g. by its fungicidal or insecticidal action which directly destroys the microorganisms or pests, but rather by a stimulation of the plants' own defensive reactions against said stress factors.

Negative factors caused by biotic stress such as pathogens and pests are widely known and are caused by living organisms, such as competing plants (for example weeds), microorganisms (such as phytopathogenic fungi and/or bacteria) and/or viruses.

Negative factors caused by abiotic stress are also well-known and can often be observed as reduced plant vigor (see above), for example: Less yield and/or less vigor, for both effects examples can be burned leaves, less flowers, premature ripening, later crop maturity, reduced nutritional value amongst others. Abiotic stress can be caused for example by: extremes in temperature such as heat or cold (heat stress/cold stress); and/or strong variations in temperature; and/or temperatures unusual for the specific season; and/or drought (drought stress); and/or extreme wetness; and/or high salinity (salt stress); and/or radiation (for example by increased UV radiation due to the decreasing ozone layer); and/or increased ozone levels (ozone stress); and/or organic pollution (for example by phythotoxic amounts of pesticides); and/or inorganic pollution (for example by heavy metal contaminants).

As a result of biotic and/or abiotic stress factors, the quantity and the quality of the stressed plants decrease. As far as quality (as defined above) is concerned, reproductive development is usually severely affected with consequences on the crops which are important for fruits or seeds. Synthesis, accumulation and storage of proteins are mostly affected by temperature; growth is slowed by almost all types of stress; polysaccharide synthesis, both structural and storage is reduced or modified: these effects result in a decrease in biomass (yield) and in changes in the nutritional value of the product.

As pointed out above, the above identified indicators for the health condition of a plant may be interdependent and may result from each other. For example, an increased resistance to biotic and/or abiotic stress may lead to a better plant vigor, e.g. to better and bigger crops, and thus to an increased yield. Inversely, a more developed root system may result in an increased resistance to biotic and/or abiotic stress. However, these interdependencies and interactions are neither all known nor fully understood and therefore the different indicators are described separately.

In one embodiment the inventive mixtures effectuate an increased yield of a plant or its product.

In another embodiment the inventive mixtures effectuate an increased vigor of a plant or its product.

In another embodiment the inventive mixtures effectuate in an increased quality of a plant or its product.

In yet another embodiment the inventive mixtures effectuate an increased tolerance and/or resistance of a plant or its product against biotic stress.

In yet another embodiment the inventive mixtures effectuate an increased tolerance and/or resistance of a plant or its product against abiotic stress.

In a preferred embodiment of the invention, the inventive mixtures effectuate an increase in the yield.

In a preferred embodiment of the invention, the inventive mixtures effect an increase in the yield.

In another preferred embodiment of the invention, the inventive mixtures effect an improvement of the plant vigor.

In another preferred embodiment of the invention, the plant health effects of the inventive mixtures effect increased resistance of plant against biotic stress.

In another preferred embodiment of the invention, the plant health effects of the inventive mixtures effect increased resistance of plant against abiotic stress.

In a more preferred embodiment of the invention, the inventive mixtures effect an increase in the yield.

In a more preferred embodiment of the invention, the inventive mixtures effect an increase in the vigor.

The mass ratio of any two ingredients in each combination is selected to give the desired, for example, synergistic action. In general, the mass ratio would vary depending on the specific compound I. Generally, the ratio by weight between any two ingredients in any combination of the present invention, independently of one another, is from 1000:1 to 1:1000, preferably from 500:1 to 1:500, more preferably the ratios from 100:1 to 1:100 (for example ratios from 99:1, 98:2, 97:3, 96:4, 95:5, 94:6, 93:7, 92:8, 91:9, 90:10, 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, 70:30, 69:31, 68:32, 67:33, 66:34, 65:45, 64:46, 63:47, 62:48, 61:49, 60:40, 59:41, 58:42, 57:43, 56:44, 55:45, 54:46, 53:47, 52:48, 51:49, 50:50, 49:51, 48:52, 47:53, 46:54, 45:55, 44:56, 43:57, 42:58, 41:59, 40:60, 39:61, 38:62, 37:63, 36:64, 35:65, 34:66, 33:67, 32:68, 31:69, 30:70, 29:71, 28:72, 27:73, 26:74, 25:75, 24:76, 23:77, 22:78, 21:79, 20:80, 19:81, 18:82, 17:83, 16:84, 15:85, 14:86, 13:87, 12:88, 11:89, 10:90, 9:91, 8:92, 7:93, 6:94, 5:95, 4:96, 3:97, 2:98, to 1:99). Herein, preferred mass ratios are those between any two components of present invention are from 75:1 to 1:75, more preferably, 50:1 to 1.50, especially 25:1 to 1:25, advantageously 10:1 to 1:10, such as 5:1 to 1:5.

These ratios are suitable for inventive mixtures applied by seed treatment, soil treatment and foliar application.

For compound II, all of these ratios refer to a preparation with at least $10^6$ CFU/g ("colony forming units per gram").

Herein, compound II may be supplied in any physiological state such as active or dormant. Dormant compound II may be supplied for example frozen, dried, or lyophilized or partly desiccated (procedures to produce these partly desiccated organisms are given in WO2008/002371) or in form of spores.

Organisms in an active state can be delivered in a growth medium without any additional additives or materials or in combination with suitable nutrient mixtures. However, the compound II is preferably delivered and formulated in a dormant stage.

In the case of mixtures comprising a further microorganism e.g. from class L), the microorganisms as used according to the invention can be cultivated continuously or discontinuously in the batch process or in the fed batch or repeated fed batch process. A review of known methods of cultivation will be found in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)). The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D. C., USA, 1981). These culture media that can be used according to the invention generally comprise one or more sources of carbon, sources of nitrogen, inorganic salts, vitamins and/or trace elements. Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid. Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as cornsteep liquor, soybean flour, soybean protein, yeast extract, meat extract and others. The sources of nitrogen can be used separately or as a mixture. Inorganic salt compounds that may be present in the media comprise the chloride, phosphate or sulfate salts of calcium, magnesium, sodium, cobalt, molybdenum, potassium, manganese, zinc, copper and iron. Inorganic sulfur-containing compounds, for example sulfates, sulfites, dithionites, tetrathionates, thiosulfates, sulfides, but also organic sulfur compounds, such as mercaptans and thiols, can be used as sources of sulfur. Phosphoric acid, potassium dihydrogenphosphate or dipotassium hydrogenphosphate or the corresponding sodium-containing salts can be used as sources of phosphorus. Chelating agents can be added to the medium, in order to keep the metal ions in solution. Especially suitable chelating agents comprise dihydroxyphenols, such as catechol or protocatechuate, or organic acids, such as citric acid. The culture media used may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (Publ. P. M. Rhodes, P. F. Stanbury, IRL Press (1997) p. 53-73, ISBN 0 19 963577 3). Growing media can also be obtained from commercial suppliers, such as Standard 1 (Merck) or BHI (Brain heart infusion, DIFCO) etc. All components of the medium are sterilized, either by heating (20 min at 2.0 bar and 121° C.) or by sterile filtration. The components can be sterilized either together, or if necessary separately. All the components of the medium can be present at the start of growing, or optionally can be added continuously or by batch feed. The temperature of the culture of the respective microorganism is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions. The temperature of the culture is normally from 20° C. to 45° C. Culture is continued until a maximum of the desired product has formed. This is normally achieved within 10 hours to 160 hours. To obtain cell-free extracts, the cells can be disrupted optionally by high-frequency ultrasound, by high pressure, e.g. in a French pressure cell, by osmolysis, by the action of detergents, lytic enzymes or organic solvents, by means of homogenizers or by a combination of several of the methods listed. The methodology of the present invention can further include a step of recovering individual compositions such as cell-free extracts, supernatants, metabolites or alike. The term "recovering" includes extracting, harvesting, isolating or purifying of an extract, supernatant or metabolite e.g. from whole culture broth. Recovering can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like. For example the agent can be recovered from culture media by first removing the microorganisms. The remaining broth is then passed through or over a cation exchange resin to remove unwanted cations and then through or over an anion exchange resin to remove unwanted inorganic anions and organic acids.

Preferred inventive mixtures are those comprising compound II and fungicidal compound IA selected from the group consisting of:

A) Respiration inhibitors

Inhibitors of complex III at Qo site (e.g. strobilurins): azoxystrobin, coumethoxy-strobin, coumoxystrobin, dimoxystrobin, enestroburin, fenaminstrobin, fenoxy-strobin/flufenoxystrobin, fluoxastro-bin, kresoxim-methyl, meto-minostrobin, orysastrobin, picoxy-strobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2(2-(3-(2,6-di-chlorophenyl)-1-methyl-allylidene-aminooxy-methyl)-phenyl)-2-methoxyimino-N methyl-acetamide, pyribencarb, triclopyricarb/chlorodin-carb, famoxadone, fenamidone;

inhibitors of complex III at Qi site: cyazofamid, amisulbrom, [(3S,6S,7R,8R)-8-beftnz-yl-3-[(3-acetoxy-4 methoxy-pyridine-2-carbonyl)amino]-6-methyl-4,9-dioxo-1,5-di-oxonan-7-yl]2 methylpropanoate, [(3S,6S,7R,8R)-8-benzyl-3-[[3-(acet-oxymeth-oxy)-4-methoxy-pyridine-2 carbonyl]amino]-6-methyl-4,9-dioxo-1,5-dioxonan-7-yl]2 methylpropanoate, [(3S,6S,7R,8R)-8-benzyl-3-[(3-isobut-oxycarbonyloxy-4-meth-oxy-pyri-dine-2 carbonyl)amino]-6-methyl-4,9-dioxo-1,5-dioxonan-7-yl]2-methylpro-panoate, [(3S,6S,7R,8R)-8-benzyl-3-[[3-(1,3-ben-zodioxol-5-yl-methoxy)-4-methoxy-pyri-dine-2-car-bonyl]amino]-6-methyl-4,9-di-oxo-1,5-dioxonan-7-yl]2-methyl-propanoate; (3S,6S,7R,8R)-3-[[(3-hydroxy-4-methoxy-2-pyridinyl)carbonyl]amino]-6 methyl-4,9-dioxo-8-(phenylmethyl)-1,5-dioxonan-7-yl2-methylpropanoate;

inhibitors of complex II (e.g. carboxamides): flutolanil, bixafen, boscalid, carboxin, fluopyram, flutolanil, fluxapyroxad, isopyrazam, oxycarboxin, penflufen, penthiopyrad, sedaxane, N-(4'-trifluoromethylthio-biphenyl-2-yl)-3 difluoromethyl-1-methyl-1H pyr-azole-4-carboxamide, N-(2-(1,3,3-trimethyl-butyl)-phenyl)-1,3-dimethyl-5 fluoro-1H-pyrazole-4 carboxamide, N-[9-(dichloromethylene)-1,2,3,4-tetrahydro-1,4-me-thanonaphthalen-5-yl]-3-(difluoromethyl)-1-methyl-1H-pyrazole-4-carboxamide (benzovindiflupyr), 3 (difluoromethyl)-1-methyl-N-(1,1,3-trimethylindan-4-yl)pyrazole-4-carboxamide, 3 (trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluorometh-yl)-1,5-dimethyl-N-(1,1,3-trimethylindan-4-yl)pyrazole-4-carboxamide, 3-(difluoro-methyl)-1,5-dimethyl-N-(1,1,3-trimethylindan-4-yl)pyrazole-4-carboxamide, 1,3,5-trhmethyl-N-(1,1,3-trimethylindan-4-yl)pyrazole-4-carboxamide;

other respiration inhibitors: (5,8-difluoro-quinazolin-4-yl)-{2-[2-fluoro-4-(4-trifluoromethylpyridin-2-yloxy)-phenyl]-ethyl}-amine, fluazinam; ametoctradin; and silthiofam;

B) Sterol biosynthesis inhibitors (SBI fungicides)

C14 demethylase inhibitors (DMI fungicides): bitertanol, cyproconazole, difenoconazole diniconazole, diniconazole-M, epoxiconazole, fluquinconazole, flusilazole, flutriafol, hexaconazole, ipconazole, metconazole, myclobutanil, propiconazole, prothio-conazole, simeconazole, tebuconazole, tetraconazole, triadimenol, triticonazole, 1-[rel-(2S;3R)-3-(2-chloro-phenyl)-2-(2,4-difluorophenyl)-oxiranylmethyl]-5 thio-cyanato-1H-[1,2,4]triazole, 2-[rel-(2S;3R)-3-(2-chlorophenyl)-2-(2,4-difluoro-phenyl)-oxiranyl-methyl]-2H[1,2,4]triazole-3-thiol, imazalil, pefurazoate, prochloraz, triflumizol;

Delta14-reductase inhibitors: fenpropimorph, spiroxamine;

C) Nucleic acid synthesis inhibitors phenylamides or acyl amino acid fungicides: benalaxyl, benalaxyl-M, kiralaxyl, metalaxyl, oxadixyl;

Others: hymexazole, oxolinic acid, 5-fluoro-2-(p-tolylmethoxy)pyrimidin-4-amine, 5-fluoro-2-(4-fluorophenylmethoxy)pyrimidin-4 amine;

D) Inhibitors of cell division and cytoskeleton tubulin inhibitors, such as benzimidazoles, thiophanates: benomyl, carbendazim, fuberidazole, thiabendazole, thiophanate-methyl;

other cell division inhibitors:, ethaboxam, pencycuron, metrafenone;

E) Inhibitors of amino acid and protein synthesis methionine synthesis inhibitors (anilino-pyrimidines): cyprodinil, pyrimethanil;

protein synthesis inhibitors: validamycin A;

F) Signal transduction inhibitors: iprodione, fludioxonil;

G) Lipid and membrane synthesis inhibitors

Phospholipid biosynthesis inhibitors: iprobenfos;

lipid peroxidation: quintozene, tolclofos-methyl, etridiazole;

phospholipid biosynthesis and cell wall deposition: dimethomorph, flumorph, pyrimorph, mandipropamid, N-(1-(1-(4-cyano-phenyl)-ethanesulfonyl)-but-2-yl)carbamic acid-(4-fluorophenyl)ester;

compounds affecting cell membrane permeability and fatty acides: propamocarb, propamo-carb-hydrochlorid H) Inhibitors with Multi Site Action inorganic active substances: Bordeaux mixture, copper acetate, copper hydroxide, copper oxychloride, basic copper sulfate, sulfur;

thio- and dithiocarbamates: ferbam, mancozeb, maneb, metiram, thiram;

organochlorine compounds (e.g. phthalimides, sulfamides, chloronitriles): chlorothalonil, captan, folpet;

guanidines and others: guanidine, dodine, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone;

I) Cell wall synthesis inhibitors: validamycin, pyroquilon, tricyclazole;

J) Plant defence inducers
acibenzolar-S-methyl, probenazole, isotianil, tiadinil, prohexadione-calcium,4-cyclopropyl-N-(2,4-dimethoxyphenyl)thiadiazole-5-carboxamide, fosetyl, fosetylaluminum;

K) Unknown mode of action: cymoxanil, flusulfamide, picarbutrazox, oxine-copper, tecloftalam, triazoxide, 2-(4-chloro-phenyl)-N[4-(3,4-dimeth¬oxy-phenyl)-isoxazol-5-yl]-2-prop-2-ynyloxy-acetamide, 4,4-difluoro-3,3-dimethyl-1-(3-quinoly)isoquinoline, 2-butoxy-6-iodo-3 propylchromen-4-one, N-(cyclo¬propylmethoxyimino-(6-difluoro-methoxy-2,3 di¬ fluoro-phenyl)-methyl)-2-phenyl acetamide, 2-methoxy-acetic acid 6-tert-butyl-8-fluoro-2,3-dimethyl-quinolin-4-yl ester, 3-[5-(4-methylphenyl)-2,3-dimethyl-isoxazolidin-3 yl]-pyridine, 3[5-(4-chlorophenyl)-2,3-dimethyl-isoxazolidin-3-yl]-pyridine (pyrisoxazole), N-(6-methoxy-pyridin-3-yl) cyclopropane¬ carboxylic acid amide, 5-chloro-1 (4,6-di¬ methoxy-pyrimidin-2-yl)-2-methyl-1H-ben¬ zoimidazole, and L) Antifungal biological Control Agents:
Ampelomyces quisqualis (e.g. AQ 10® from Intrachem Bio GmbH & Co. KG, Germany), Aspergillus flavus (e.g. AFLAGUARD® from Syngenta, CH), Aureobasidium pullulans (e.g. BOTECTOR® from bio-ferm GmbH, Germany), Bacillus pumilus (e.g. NRRL Accession No. B-30087 in SONATA® and BALLAD® Plus from AgraQuest Inc., USA), Bacillus subtilis (e.g. isolate NRRL-Dr. B-21661 in RHAPSODY®, SERENADE® MAX and SERENADE® ALSO from AgraQuest Inc., USA), Bacillus subtilis var. amyloliguefaciens FIB24 (e.g. TARO® from Novozyme Biologicals, Inc., USA), Candida oleophila I-82 (e.g. ASPIRE® from Ecogen Inc., USA), Candida saitoana (e.g. BIOCURE® (in mixture with lysozyme) and BIO-COAT® from Micro Flo Company, USA (BASF SE) and Arysta), Chitosan (e.g. ARMOUR-ZEN from BotriZen Ltd., NZ), Clonostachys rosea f. catenulata, also named Gliocladium catenulatum (e.g. isolate J1446: PRESTOP® from Verdera, Finland), Coniothyrium minitans (e.g. CONTANS® from Prophyta, Germany), Cryphonectria parasitica (e.g. Endothia parasitica from CNICM, France), Cryptococcus albidus (e.g. YIELD PLUS® from Anchor Bio-Technologies, South Africa), Fusarium oxysporum (e.g. BIOFOX® from S.I.A.P.A., Italy, FUSACLEAN® from Natural Plant Protection, France), Metschnikowia fructicola (e.g. SHEMER® from Agrogreen, Israel), Microdochium dimerum (e.g. ANTI BOT® from Agrauxine, France), Phlebiopsis gigantea (e.g. ROTSOP® from Verdera, Finland), Pseudozyma flocculosa (e.g. SPORODEX® from Plant Products Co. Ltd., Canada), Pythium oligandrum DV74 (e.g. POLYVERSUM® from Remeslo SSRO, Biopreparaty, Czech Rep.), Reynoutria sachlinensis (e.g. REGALIA® from Marrone Biolnnovations, USA), Talaromyces flavus V117b (e.g. PROTUS® from Prophyta, Germany), Trichoderma asperellum SKT-1 (e.g. ECO-HOPE® from Kumiai Chemical Industry Co., Ltd., Japan), T. atroviride LC52 (e.g. SENTINEL® from Agrimm Technologies Ltd, NZ), T. harzianum T-22 (e.g. PLANT-SHIELD® der Firma BioWorks Inc., USA), T. harzianum TH 35 (e.g. ROOT PRO® from Mycontrol Ltd., Israel), T. harzianum T-39 (e.g. TRICHODEX® and TRICHODERMA 2000® from Mycontrol Ltd., Israel and Makhteshim Ltd., Israel), T. harzianum and T. viride (e.g. TRICHOPEL from Agrimm Technologies Ltd, NZ), T. harzianum ICC012 and T. viride ICC080 (e.g. REMEDIER® WP from Isagro Ricerca, Italy), T. polysporum and T. harzianum (e.g. BINAB® from BINAB Bio-Innovation AB, Sweden), T. stromaticum (e.g. TRICOVAB® from C.E.P.L.A.C., Brazil), T. virens GL-21 (e.g. SOILGARD® from Certis LLC, USA), T. viride (e.g. TRIECO® from Ecosense Labs. (India) Pvt. Ltd., Indien, BIO-CURE® F from T. Stanes & Co. Ltd., Indien), T. viride TV1 (e.g. T. viride TV1 from Agribiotec srl, Italy), Ulocladium oudemansii HRU3 (e.g. BOTRY-ZEN® from Botry-Zen Ltd, NZ).

Equally preferred inventive mixtures are those comprising compound II and insecticidal compound IB selected from the group consisting of:

M-1A acetylcholine esterase inhibitors from the class of carbamates: aldicarb, benfuracarb, carbofuran, carbosulfan, isoprocarb, methiocarb, methomyl, oxamyl, pirimicarb, thiodicarb, triazamate;

M-1B acetylcholine esterase inhibitors from the class of organophosphates: acephate, cadusafos, chlorethoxyfos, chlorfenvinphos, chlorpyrifos, chlorpyrifos-methyl, diazinon, dichlorvos/DDVP, dimethoate, disulfoton, ethoprophos, fenamiphos, fenitrothion, imicyafos, isofenphos, methamidophos, phoxim, profenofos, tebupirimfos, terbufos, chlormephos, fosthiazate, isoxathion, phorate, pirimiphos-methyl;

M-2 GABA-gated chloride channel antagonists:
M-2A fiprole (phenylpyrazoles): ethiprole, fipronil, flufiprole, pyrafluprole, or pyriprole;

M-2B Others: 4-[5-[3-chloro-5-(trifluoromethyl)phenyl]-5-(trifluoromethyl)-4H-isoxazol-3-yl]-N-[2-oxo-2-(2,2,2-trifluoroethylamino)ethyl]naphthalene-1-carboxamide (known from WO 2007/079162) or the compound 4-[5-(3,5-dichlorophenyl)-5-(trifluoromethyl)-4H-isoxazol-3-yl]-2-methyl-N42-oxo-2-(2,2,2-trifluoroethylamino)ethypenzamide (known from WO 05/085216);

M-3 sodium channel modulators from the class of pyrethroids: bifenthrin, cyfluthrin, beta-cyfluthrin, lambda-cyhalothrin, cypermethrin, alpha-cypermethrin, zetacypermethrin, deltamethrin, esfenvalerate, etofenprox, fenvalerate, flucythrinate, permethrin, tefluthrin, acrinathrin, allethrin, d-cis-trans allethrin, d-trans allethrin, bioalle-thrin, bioallethrin S-cylclopentenyl, bioresmethrin, cycloprothrin, cyhalothrin, gamma-cyhalothrin, beta-cypermethrin, theta-cypermethrin, silafluofen;

M-4 nicotinic acteylcholine receptor agonists from the class of neonicotinoids: acteamiprid, chlothianidin, cycloxaprid, dinotefuran, flupyradifurone, imidacloprid, nitenpyram, sulfoxaflor, thiacloprid, thiamethoxam or the compound 1-[(6-chloro-3-pyridyl)methyl]-7-methyl-8-nitro-5-propoxy-3,5,6,7-tetrahydro-2H-imidazo[1,2-a]pyridine (known from WO 2007/101369);

M-5 allosteric nicotinic acetylcholine receptor activators from the class of spinosyns: spinosad, spinetoram;

M-6 chloride channel activators from the class of mectins: abamectin, emamectin benzoate, ivermectin, lepimectin or milbemectin;

M-9 selective homopteran feeding blockers: pymetrozine, pyrifluquinazon, 2-(5-fluoro-3-pyridyl)-5-(6-pyrimid in-2-yl-2-pyridyl)thiazole hydrofluoride;

M-12 uncouplers of oxidative phosphorylation: chlorfenapyr;

M-13 nicotinic acetylcholine receptor channel blockers: cartap hydrochloride;

M-14 inhibitors of the chitin biosynthesis type 0 (benzoylurea class): diflubenzuron, flufenoxuron, lufenuron, novaluron, teflubenzuron;

M-15 inhibitors of the chitin biosynthesis type 1: buprofezin;

M-17 Ecdyson receptor agonists: methoxyfenozide;

M-20 Mitochondrial complex I electron transport inhibitors: tebufenpyrad;

M-21 Voltage-dependent sodium channel blockers: indoxacarb or metaflumizone;

M-22 Inhibitors of the lipid synthesis, inhibitors of acetyl CoA carboxylase: spirodiclofen, spirotetramat;

M-24 Ryanodine receptor-modulators from the class of diamides: flubendiamide, chloranthraniliprole (rynaxypyr), cyanthraniliprole (cyazypyr), the phthalamide compounds (R)-3-Chlor-N1-{2-methyl-4-[1,2,2,2-tetrafluor-1-(trifluormethyl)ethyl]phenyl}-N2-(1-methyl-2-methylsulfonyl-ethyl)phthalamid or (S)-3-Chlor-N1-{2-methyl-4-[1,2,2,2-tetrafluor-1-(trifluormethypethyl]phenyl}-N2-(1-methyl-2-methylsulfonylethyl)phthalamid (both known from WO 2007/101540), the compound 3-bromo-N-{2-bromo-4-chloro-6-[(1-cyclopropylethyl)carbamoyl]phenyl}-1-(3-chlorpyridin-2-yl)-1H-pyrazole-5-carboxamide (known from WO 2005/077934), the compound methyl-2-[3,5-di-bromo-2-({[3-bromo-1-(3-chlorpyridin-2-yl)-1H-pyrazol-5-yl]carbonyl}amino)benzoyl]-1,2-dimethylhydrazinecarboxylate (known from WO 2007/043677), N2-[2-(3-chloro-2-pyridyl)-5-[(5-methyltetrazol-2-yl)methyl]pyrazol-3-yl]-5-cyano-N1,3-dimethyl-phthalamide (known from WO 2007/144100)

M-25 Others: afidopyropen, 2-(5-ethylsulfinyl-2-fluoro-4-methyl-phenyl)-5-methyl-1,2,4-triazol-3-amine (known from WO 06/043635), 1-(5-ethylsulfinyl-2,4-dimethyl-phenyl)-3-methyl-1,2,4-triazole (known from WO 06/043635) and metaldehyde, and M-26: *Bacillus firmus* (e.g. *Bacillus firmus* CNCM 1-1582, e.g. WO09126473A1 and WO09124707 A2, commercially available as "Votivo")

More preferred inventive mixtures are those comprising compound II and fungicidal compound IA displayed in Table 1A:

In Table 1A, the following abbreviations are used:
*Beauveria bassiana* PPRI 5339=A
IA=Comopund IA II=Compoound II

| No | IA | II |
|---|---|---|
| M-1. | azoxystrobin | A |
| M-2. | dimoxystrobin | A |
| M-3. | fluoxastrobin | A |
| M-4. | kresoxim-methyl | A |
| M-5. | orysastrobin | A |
| M-6. | picoxystrobin | A |
| M-7. | pyraclostrobin | A |
| M-8. | trifloxystrobin | A |
| M-9. | pyribencarb | A |
| M-10. | cyazofamid | A |
| M-11. | amisulbrom | A |
| M-12. | [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate | A |
| M-13. | [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate | A |
| M-14. | [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate | A |
| M-15. | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate | A |
| M-16. | bixafen | A |
| M-17. | boscalid | A |
| M-18. | carboxin | A |
| M-19. | fluopyram | A |
| M-20. | fluxapyroxad | A |
| M-21. | isopyrazam | A |
| M-22. | penflufen | A |
| M-23. | penthiopyrad | A |
| M-24. | sedaxane | A |
| M-25. | N-(4'-trifluoromethylthiobiphenyl-2-yl)-3-difluoromethyl-1-methyl-1H-pyrazole-4-carboxamide | A |
| M-26. | N-(2-(1,3,3-trimethylbutyl)-phenyl)-1,3-dimethyl-5-fluoro-1H-pyrazole-4-carboxamide | A |
| M-27. | N-[9-(dichloromethylene)-1,2,3,4-tetrahydro-1,4-methanonaphthalen-5-yl]-3-(difluoromethyl)-1-methyl-1H-pyrazole-4-carboxamide (benzovindiflupyr) | A |
| M-28. | 3-(difluoromethyl)-1-methyl-N-(1,1,3-trimethylindan-4-yl)pyrazole-4-carboxamide | A |
| M-29. | 3-(trifluoromethyl)-1-methyl-N-(1,1,3-trimethylindan-4-yl)pyrazole-4-carboxamide | A |
| M-30. | 1,3-dimethyl-N-(1,1,3-trimethylindan-4-yl)pyrazole-4-carboxamide | A |
| M-31. | 3-(trifluoromethyl)-1,5-dimethyl-N-(1,1,3-trimethylindan-4-yl)pyrazole-4-carboxamide | A |
| M-32. | 3-(difluoromethyl)-1,5-dimethyl-N-(1,1,3-trimethylindan-4-yl)pyrazole-4-carboxamide | A |
| M-33. | 1,3,5-trimethyl-N-(1,1,3-trimethylindan-4-yl)pyrazole-4-carboxamide | A |
| M-34. | (5,8-difluoroquinazolin-4-yl)-{2-[2-fluoro-4-(4-trifluoromethylpyridin-2-yloxy)-phenyl]-ethyl}-amine | A |
| M-35. | ametoctradin | A |
| M-36. | silthiofam | A |
| M-37. | cyproconazole | A |
| M-38. | difenoconazole | A |
| M-39. | epoxiconazole | A |
| M-40. | fluquinconazole | A |
| M-41. | ipconazole | A |
| M-42. | metconazole | A |
| M-43. | propiconazole | A |
| M-44. | prothioconazole | A |
| M-45. | tebuconazole | A |
| M-46. | triadimenol | A |
| M-47. | triticonazole, | A |
| M-48. | 1-[rel-(2S;3R)-3-(2-chlorophenyl)-2-(2,4-difluorophenyl)-oxiranylmethyl]-5-thiocyanato-1H-[1,2,4]triazole | A |
| M-49. | 2-[rel-(2S;3R)-3-(2-chlorophenyl)-2-(2,4-difluorophenyl)-oxiranylmethyl]-2H-[1,2,4]triazole-3-thiol | A |
| M-50. | prochloraz | A |
| M-51. | fenpropimorph | A |
| M-52. | benalaxyl | A |
| M-53. | benalaxyl-M | A |
| M-54. | kiralaxyl | A |
| M-55. | metalaxyl | A |
| M-56. | 5-fluoro-2-(p-tolylmethoxy)pyrimidin-4-amine | A |
| M-57. | 5-fluoro-2-(4-fluorophenylmethoxy)pyrimidin-4-amine | A |
| M-58. | hymexazole | A |
| M-59. | carbendazim | A |
| M-60. | thiabendazole | A |
| M-61. | thiophanate-methyl | A |

| No | IA | II |
|---|---|---|
| M-62. | ethaboxam | A |
| M-63. | metrafenone, | A |
| M-64. | cyprodinil | A |
| M-65. | pyrimethanil | A |
| M-66. | fludioxonil | A |
| M-67. | iprodione | A |
| M-68. | dimethomorph | A |
| M-69. | flumorph | A |
| M-70. | mandipropamid | A |
| M-71. | N-(1-(1-(4-cyanophenyl)ethanesulfonyl)-but-2-yl) carbamic acid-(4-fluorophenyl) ester | A |
| M-72. | mancozeb | A |
| M-73. | maneb | A |
| M-74. | metiram | A |
| M-75. | thiram | A |
| M-76. | chlorothalonil | A |
| M-77. | captan | A |
| M-78. | dithianon | A |
| M-79. | 2,6-dimethyl-1H,5H-[1,4]dithiino[2,3-c:5,6-c']di-pyrrole-1,3,5,7(2H,6H)-tetraone | A |
| M-80. | isotianil | A |
| M-81. | tiadinil | A |
| M-82. | prohexadione-calcium | A |
| M-83. | 4-cyclopropyl-N-(2,4-dimethoxy-phenyl)thiadiazole-5-carboxamide | A |
| M-84. | triazoxide | A |
| M-85. | 2-(4-chloro-phenyl)-N-[4-(3,4-dimethoxyphenyl)-isoxazol-5-yl]-2-prop-2-ynyloxyacetamide | A |
| M-86. | 4,4-difluoro-3,3-dimethyl-1-(3-quinolyl)isoquinoline | A |
| M-87. | 2-butoxy-6-iodo-3-propylchromen-4-one | A |
| M-88. | N-(cyclopropylmethoxyimino-(6-difluoro-methoxy-2,3-difluoro-phenyl)-methyl)-2-phenyl acetamide | A |
| M-89. | 2-methoxy-acetic acid 6-tert-butyl-8-fluoro-2,3-dimethyl-quinolin-4-yl ester | A |
| M-90. | 3-[5-(4-methylphenyl)-2,3-dimethyl-isoxazolidin-3-yl]-pyridine | A |
| M-91. | 3-[5-(4-chloro-phenyl)-2,3-dimethyl-isoxazolidin-3-yl]-pyridine (pyrisoxazole) | A |
| M-92. | N-(6-methoxy-pyridin-3-yl) cyclopropane-carboxylic acid amide | A |
| M-93. | 5-chloro-1-(4,6-dimethoxy-pyrimidin-2-yl)-2-methyl-1H-benzoimidazole. | A |
| M-94. | bitertanol | |
| M-95. | diniconazole | |
| M-96. | diniconazole-M | |
| M-97. | flutriafol | |
| M-98. | hexaconazole | |
| M-99. | triflumizol | |
| M-100. | oxadixyl | |
| M-101. | validamycin A | |
| M-102. | probenfos | |
| M-103. | quintozene | |
| M-104. | tolclofos-methyl | |
| M-105. | validamycin | |
| M-106. | isotianil | |
| M-107. | fosetyl | |
| M-108. | flusulfamide | |
| M-109. | *Ampelomyces quisqualis* | A |
| M-110. | *Aspergillus flavus* | A |
| M-111. | *Aureobasidium pullulans* | A |
| M-112. | *Bacillus pumilus* | A |
| M-113. | *Bacillus pumilus* NRRL Accession No. B-30087 | A |
| M-114. | *Bacillus subtilis* | A |
| M-115. | *Bacillus subtilis* NRRL-Nr. B-21661 | A |
| M-116. | *Bacillus subtilis* var. *amyloliquefaciens* FZB24 | A |
| M-117. | *Candida oleophila* I-82 | A |
| M-118. | *Candida saitoana* | A |
| M-119. | Chitosan | A |
| M-120. | *Clonostachys rosea* f. *catenulate* | A |
| M-121. | *Clonostachys rosea* f. *catenulate* isolate J1446 | A |
| M-122. | *Coniothyrium minitans* | A |
| M-123. | *Cryphonectria parasitica* | A |
| M-124. | *Endothia parasitica* | A |
| M-125. | *Cryptococcus albidus* | A |
| M-126. | *Fusarium oxysporum* | A |
| M-127. | FUSACLEAN ® | A |
| M-128. | *Metschnikowia fructicola* | A |
| M-129. | *Microdochium dimerum* | A |
| M-130. | *Phlebiopsis gigantea* | A |
| M-131. | *Pseudozyma flocculosa* | A |
| M-132. | *Pythium oligandrum* DV74 | A |
| M-133. | *Reynoutria sachlinensis* | A |
| M-134. | *Talaromyces flavus* V117b | A |
| M-135. | *Trichoderma asperellum* SKT-1 | A |
| M-136. | *T. atroviride* LC52 | A |
| M-137. | *T. harzianum* T-22 | A |
| M-138. | *T. harzianum* TH 35 | A |
| M-139. | *T. harzianum* T-39 | A |
| M-140. | *T. harzianum* and *T. viride* | A |
| M-141. | *T. harzianum* ICC012 and *T. viride* ICC080 | A |
| M-142. | *T. polysporum* and *T. harzianum* | A |
| M-143. | *T. stromaticum* | A |
| M-144. | *T. virens* GL-21 | A |
| M-145. | *T. viride* | A |
| M-146. | *T. viride* TV1 | A |
| M-147. | *Ulocladium oudemansii* HRU3 | A |
| M-148. | flutolanil | A |

Table 1A-01

Equally more preferred mixtures are mixtures N-1 to N-148, comprising *Metarhizium anisopliae* FI-1045 as compound II instead of "A" and compound IA corresponding to M-1 to M-148 as defined in Table 1A.

Table 1A-02

Equally more preferred mixtures are mixtures O-1 bis O-148, comprising *Metarhizium anisopliae* var. *acridum* IMI 330189 as compound II instead of "A" and compound IA corresponding to M-1 to M-148 as defined in Table 1A.

Table 1A-03

Equally more preferred mixtures are mixtures P-1 bis P-148, comprising *Metarhizium anisopliae* var. *acridum* FI-985 as compound II instead of "A" and compound IA corresponding to M-1 to M-148 as defined in Table 1A.

Preferred inventive mixtures especially useful for seed treatment are those comprising compound II and fungicidal compound IA selected from Pyraclostrobin, Azoxystrobin, Trifloxystrobin, Picoxystrobin, Boscalid, Fluoxapyroxad, Fluopyram, Penflufen, Benzovindiflupyr, Sedaxane, Penthiopyrad, Difenoconazole, Fluquinconazole, Triticonazole, Tebuconazole, Tetraconazole, Hexaconazole, Thiophanate-methyl, Pyrimethanil, Cyrodinil, Metalaxyl, Dimethomorph and Mandiprpamid; more preferably selected from Pyraclostrobin, Azoxystrobin, Trifloxystrobin, Picoxystrobin, Boscalid, Fluoxapyroxad, Fluopyram, Penflufen, Benzovindiflupyr, Sedaxane, Penthiopyrad, Difenoconazole, Fluquinconazole, Triticonazole, Tebuconazole, Tetraconazole, Hexaconazole and Thiophanate-methyl.

Preferred inventive mixtures especially useful for soil treatment are those comprising compound II and fungicidal compound IA selected from Pyraclostrobin, Azoxystrobin, Trifloxystrobin, Picoxystrobin, Fluoxapyroxad, Fluopyram, Benzovindiflupyr, Metalaxyl, Fludioxonil, Oryzastrobin, Boscalid, Penthiopyrad, Iprodione, Dimethomorph and Mandipropamid, more preferably selected from Pyraclostrobin, Azoxystrobin, Trifloxystrobin, Picoxystrobin, Fluoxapyroxad, Fluopyram, Benzovindiflupyr, Metalaxyl and Fludioxonil.

Preferred inventive mixtures especially useful for foliar treatment are those comprising compound II and fungicidal compound IA selected from Dimoxystrobin, Pyraclostrobin, Azoxystrobin, Trifloxystrobin, Picoxystrobin, Cyazofamid, Boscalid, Fluoxapyroxad, Fluopyram, Bixafen, Isopyrazam, Benzovindiflupyr, Penthiopyrad, Ametoctradin, Difenoconazole, Metconazole, Prothioconazole, Tebuconazole, Propiconazole, Cyproconazole, Penconazole, Myclobutanil, Tetraconazole, Hexaconazole, Metrafenone, Zoxamid, Pyrimethanil, Cyprodinil, Metalaxyl, Fludioxonil, Dimethomorph, Mandipropamid, Tricyclazole, Copper, Metiram, Chlorothalonil, Dithianon, Fluazinam, Folpet, Fosetyl-Al, Captan, Cymoxanil, Mancozeb, Kresoxim-methyl, Oryzastrobin, Epoxiconazole, Fluquinconazole, Triticonazole, Fenpropimorph and Iprodione; more preferably selected from Dimoxystrobin, Pyraclostrobin, Azoxystrobin, Trifloxystrobin, Picoxystrobin, Cyazofamid, Boscalid, Fluoxapyroxad, Fluopyram, Bixafen, Isopyrazam, Benzovindiflupyr, Penthiopyrad, Ametoctradin, Difenoconazole, Metconazole, Prothioconazole, Tebuconazole, Propiconazole, Cyproconazole, Penconazole, Myclobutanil, Tetraconazole, Hexaconazole, Metrafenone, Zoxamid, Pyrimethanil, Cyprodinil, Metalaxyl, Fludioxonil, Dimethomorph, Mandipropamid, Tricyclazole, Copper, Metiram, Chlorothalonil, Dithianon, Fluazinam, Folpet, Fosetyl-Al, Captan, Cymoxanil and Mancozeb.

Equally more preferred mixtures are those comprising compound II and compound IB displayed in Table 1B:

In Table 1B, the following abbreviations are used:
*Beauveria bassiana* PPRI 5339=A
IB=Compound IB II=Compound II

| No | IB | II |
|---|---|---|
| M'-1. | carbofuran | A |
| M'-2. | carbosulfan | A |
| M'-3. | methiocarb | A |
| M'-4. | methomyl | A |
| M'-5. | thiodicarb | A |
| M'-6. | triazamate | A |
| M'-7. | acephate | A |
| M'-8. | chlorpyrifos | A |
| M'-9. | chlorpyrifos-methyl | A |
| M'-10. | dimethoate | A |
| M'-11. | methamidophos | A |
| M'-12. | ethiprole | A |
| M'-13. | fipronil | A |
| M'-14. | 4-[5-[3-chloro-5-(trifluoromethyl)phenyl]-5-(trifluoromethyl)-4H-isoxazol-3-yl]-N-[2-oxo-2-(2,2,2-trifluoroethylamino)ethyl]naphthalene-1-carboxamide | A |
| M'-15. | 4-[5-(3,5-dichlorophenyl)-5-(trifluoromethyl)-4H-isoxazol-3-yl]-2-methyl-N-[2-oxo-2-(2,2,2-trifluoroethylamino)ethyl]benzamide | A |
| M'-16. | bifenthrin | A |
| M'-17. | cyfluthrin | A |
| M'-18. | beta-cyfluthrin | A |
| M'-19. | lambda-cyhalothrin | A |
| M'-20. | cypermethrin | A |
| M'-21. | alpha-cypermethrin | A |
| M'-22. | zeta-cypermethrin | A |
| M'-23. | deltamethrin | A |
| M'-24. | fenvalerate | A |
| M'-25. | flucythrinate | A |
| M'-26. | permethrin | A |
| M'-27. | tefluthrin | A |
| M'-28. | acteamiprid | A |
| M'-29. | chlothianidin | A |
| M'-30. | cycloxaprid | A |
| M'-31. | dinotefuran | A |
| M'-32. | flupyradifurone | A |
| M'-33. | imidacloprid | A |
| M'-34. | nitenpyram | A |
| M'-35. | sulfoxaflor | A |
| M'-36. | thiacloprid | A |
| M'-37. | thiamethoxam | A |
| M'-38. | 1-[(6-chloro-3-pyridyl)methyl]-7-methyl-8-nitro-5-propoxy-3,5,6,7-tetrahydro-2H-imidazo[1,2-a]pyridine | A |
| M'-39. | spinosad | A |
| M'-40. | spinetoram | A |
| M'-41. | abamectin | A |
| M'-42. | emamectin benzoate | A |
| M'-43. | 2-(5-fluoro-3-pyridyl)-5-(6-pyrimidin-2-yl-2-pyridyl)thiazole hydrofluoride | A |
| M'-44. | chlorfenapyr | A |
| M'-45. | diflubenzuron | A |
| M'-46. | flufenoxuron | A |
| M'-47. | novaluron | A |
| M'-48. | teflubenzuron | A |
| M'-49. | tebufenpyrad | A |
| M'-50. | indoxacarb | A |
| M'-51. | metaflumizone | A |
| M'-52. | flubendiamide | A |
| M'-53. | chloranthraniliprole (rynaxypyr) | A |
| M'-54. | cyanthraniliprole (cyazypyr) | A |
| M'-55. | (R)-3-Chlor-N1-{2-methyl-4-[1,2,2,2-tetrafluor-1-(trifluormethyl)ethyl]phenyl}-N2-(1-methyl-2-methylsulfonylethyl)phthalamid | A |
| M'-56. | (S)-3-Chlor-N1-{2-methyl-4-[1,2,2,2-tetrafluor-1-(trifluormethyl)ethyl]phenyl}-N2-(1-methyl-2-methyl-sulfonylethyl)phthalamid | A |
| M'-57. | 3-bromo-N-{2-bromo-4-chloro-6-[(1-cyclopropylethyl)carbamoyl]phenyl}-1-(3-chlorpyridin-2-yl)-1H-pyrazole-5-carboxamide | A |
| M'-58. | methyl-2-[3,5-dibromo-2-({[3-bromo-1-(3-chlor-pyridin-2-yl)-1H-pyrazol-5-yl]carbonyl}amino)benzoyl]-1,2-dimethylhydrazinecarboxylate | A |
| M'-59. | N2-[2-(3-chloro-2-pyridyl)-5-[(5-methyltetrazol-2-yl)methyl]pyrazol-3-yl]-5-cyano-N1,3-dimethyl-phthalamide | A |
| M'-60. | 2-(5-ethylsulfinyl-2-fluoro-4-methyl-phenyl)-5-methyl-1,2,4-triazol-3-amine | A |
| M'-61. | 1-(5-ethylsulfinyl-2,4-dimethyl-phenyl)-3-methyl-1,2,4-triazole | A |
| M'-62. | afidopyropen | A |
| M'-63. | aldicarb | A |
| M'-64. | benfuracarb | A |
| M'-65. | isoprocarb | A |
| M'-66. | oxamyl | A |
| M'-67. | pirimicarb | A |
| M'-68. | cadusafos | A |
| M'-69. | chlorethoxyfos | A |
| M'-70. | chlorfenvinphos | A |
| M'-71. | chlormephos | A |
| M'-72. | dichlorvos/DDVP | A |
| M'-73. | disulfoton | A |
| M'-74. | ethoprophos | A |
| M'-75. | fenamiphos | A |
| M'-76. | fosthiazate | A |
| M'-77. | imicyafos | A |
| M'-78. | isofenphos | A |
| M'-79. | isoxathion | A |
| M'-80. | phorate | A |
| M'-81. | pirimiphos-methyl | A |
| M'-82. | tebupirimfos | A |
| M'-83. | terbufos | A |
| M'-84. | pyriprole | A |
| M'-85. | silafluofen | A |
| M'-86. | metaldehyde | A |
| M'-87. | *Bacillus firmus* | A |
| M'-88. | *Bacillus firmus* of strain CNCM 1-1582 | A |

Table 1B-01

Equally more preferred mixtures are mixtures N'-1 to N'-88, comprising *Metarhizium anisopliae* FI-1045 as compound II instead of "A" and compound IB corresponding to M'-1 to M'-88 as defined in Table 1B.

Table 1 B-02

Equally more preferred mixtures are mixtures O'-1 to O'-88, comprising *Metarhizium anisopliae* var. *acridum* strain IMI 330189 as compound II instead of "A" and compound IB corresponding to M'-1 to M'-88 as defined in Table 1B.

Table 1B-03

Equally more preferred mixtures are mixtures P'-1 to P'-88, comprising *Metarhizium anisopliae* var. *acridum* strain FI-985 as compound II instead of "A" and compound IB corresponding to M'-1 to M'-88 as defined in Table 1B.

More preferred inventive mixtures are those comprising compound II and insecticidal compound IB selected from momfluorothrin; 1-[(6-chloro-3-pyridyl)methyl]-2-nitro-1-[(E)-pentylideneamino]guanidine; 1-[(E)-[2-(4-cyanophenyl)-1-[3-(trifluoromethyl)phenyl]ethylidene]amino]-3-[4-(difluoromethoxy)phenyl]urea; N2-(1-cyano-1-methyl-ethyl)-N1-(2,4-dimethylphenyl)-3-iodo-phthalamide, 3-chloro-N2-(1-cyano-1-methyl-ethyl)-N1-(2,4-dimethylphenyl)phthalamide, 2-(3-chloro-2-pyridyl)-N-[4-cyano-2-methyl-6-(methylcarbamoyl)phenyl]-5-[[5-(trifluoromethyl)tetrazol-2-yl]methyl]pyrazole-3-carboxamide, N-[2-(tert-butylcarbamoyl)-4-chloro-6-methyl-phenyl]-2-(3-chloro-2-pyridyl)-5-(fluoromethoxy)pyrazole-3-carboxamide, 5-bromo-N-[2,4-dichloro-6-(methylcarbamoyl)phenyl]-2-(3,5-dichloro-2-pyridyl) pyrazole-3-carboxamide, 5-chloro-2-(3-chloro-2-pyridyl)-N-[2,4-dichloro-6-[(1-cyano-1-methyl-ethyl)car-bamoyl]phenyl]pyrazole-3-carboxamide, N-[2-(5-amino-1,3,4-thiadiazol-2-yl)-4-chloro-6-methyl-phenyl]-5-bromo-2-(3-chloro-2-pyridyl)pyrazole-3-carboxamide; triflumezopyrim, 8-chloro-N-[2-chloro-5-methoxyphenyl)sulfonyl]-6-trifluoromethyl)-imidazo[1,2-a]pyridine-2-carboxamide, 5-[3-[2,6-dichloro-4-(3,3-dichloroallyloxy)phenoxy]propoxy]-1H-pyrazole, N-[1-[(6-chloro-3-pyridyl)methyl]-2-pyridylidene]-2,2,2-trifluoro-acetamide, N-[1-[(6-chloro-3-pyridyl)methyl]-2-pyridylidene]-2,2,3,3,3-pentafluoropropanamide, N-[1-[(6-bromo-3-pyridyl)methyl]-2-pyridylidene]-2,2,2-trifluoro-acetamide, N-[1-[(2-chloropyrimidin-5-yl)methyl]-2-pyridylidene]-2,2,2-trifluoro-acetamide, N-[1-[(6-chloro-5-fluoro-3-pyridyl)methyl]-2-pyridylidene]-2,2,2-trifluoro-acetamide, 2,2,2-trifluoro-N-[1-[(6-fluoro-3-pyridyl)methyl]-2-pyridylidene]acetamide, 2-chloro-N-[1-[(6-chloro-3-pyridyl)methyl]-2-pyridylidene]-2,2-difluoro-acetamide, N-[1-[1-(6-chloro-3-pyridyl)ethyl]-2-pyridylidene]-2,2,2-trifluoro-acetamide, N-[1-[(6-chloro-3-pyridyl)methyl]-2-pyridylidene]-2,2-difluoro-acetamide; 11-(4-chloro-2,6-dimethylphenyl)-12-hydroxy-1,4-dioxa-9-azadispiro[4.2.4.2]-tetradec-11-en-10-one, 3-(4'-fluoro-2,4-dimethylbiphenyl-3-yl)-4-hydroxy-8-oxa-1-azaspiro[4.5]dec-3-en-2-one, 2-(5-fluoro-3-pyridyl)-5-(6-pyrimidin-2-yl-2-pyridyl)thiazole hydrofluoride, 2-(3-pyridyl)-5-(6-pyrimidin-2-yl-2-pyridyl)thiazole, 5-[6-(1,3-dioxan-2-yl)-2-pyridyl]-2-(3-pyridyl)thiazole, 4-[5-[3-chloro-5-(trifluoromethyl)phenyl]-5-(trifluoromethyl)-4H-isoxazol-3-yl]-N-[2-oxo-2-(2,2,2-trifluoroethylamino)ethyl]naphthal-ene-1-carboxamide, 4-[5-(3,5-dichlorophenyl)-5-(trifluoromethyl)-4H-isoxazol-3-yl]-2-methyl-N-[2-oxo-2-(2,2,2-trifluoroethylamino)ethyl]benzamide and 4-[5-(3,5-dichlorophenyl)-5-(trifluoromethyl)-4H-isoxazol-3-yl]-2-methyl-N-(1-oxothietan-3-yl)benzamide.

Equally more preferred inventive mixtures are those comprising compound II and compound IC having plant growth regulating activity displayed in Table 1C:

In Table 1C, the following abbreviations are used:
*Beauveria bassiana* PPRI 5339=A
IC=Compound IC  II=Compound II

| No | IC | II |
|---|---|---|
| M"-1. | abscisic acid | A |
| M"-2. | amidochlor | A |
| M"-3. | ancymidol | A |
| M"-4. | 6-benzylaminopurine | A |
| M"-5. | brassinolide | A |

-continued

| No | IC | II |
|---|---|---|
| M"-6. | butralin | A |
| M"-7. | chlormequat (chlormequat chloride) | A |
| M"-8. | choline chloride | A |
| M"-9. | cyclanilide | A |
| M"-10. | daminozide | A |
| M"-11. | dike-gulac | A |
| M"-12. | dimethipin | A |
| M"-13. | 2,6-dimethylpuridine | A |
| M"-14. | ethephon | A |
| M"-15. | flumetralin | A |
| M"-16. | flurprimidol | A |
| M"-17. | fluthiacet | A |
| M"-18. | forchlorfenuron | A |
| M"-19. | gibberellic acid | A |
| M"-20. | inabenfide | A |
| M"-21. | indole-3-acetic acid | A |
| M"-22. | maleic hydrazide | A |
| M"-23. | mefluidide | A |
| M"-24. | mepiquat (mepiquat chloride) | A |
| M"-25. | naphthaleneacetic acid | A |
| M"-26. | N-6-benzyladenine | A |
| M"-27. | paclobutrazol | A |
| M"-28. | prohexadione (prohexadione-calcium) | A |
| M"-29. | prohydrojasmon | A |
| M"-30. | thidiazuron | A |
| M"-31. | triapenthenol | A |
| M"-32. | tributyl phosphorotrithioate | A |
| M"-33. | 2,3,5-triiodobenzoic acid | A |
| M"-34. | trinexapac-ethyl | A |
| M"-35. | uniconazole | A |

Table 1C-01

Equally more preferred mixtures are mixtures N"-1 to N"-88, comprising *Metarhizium anisopliae* FI-1045 as compound II instead of "A" and compound IC corresponding to M"-1 to M"-88 as defined in Table 1C.

Table 1C-02

Equally more preferred mixtures are mixtures O"-1 to O"-88, comprising *Metarhizium anisopliae* var. *acridum* strain IMI 330189 as compound II instead of "A" and compound IC corresponding to M"-1 to M"-88 as defined in Table 1C.

Table 1C-03

Equally more preferred mixtures are mixtures P"-1 to P"-88, comprising *Metarhizium anisopliae* var. *acridum* strain FI-985 as compound II instead of "A" and compound IC corresponding to M"-1 to M"-88 as defined in Table 1C.

More preferred inventive mixtures especially useful for seed treatment are those comprising compound II and compound IC having plant growth regulating activity selected from 6-benzylaminopurine (=N-6-benzyladenine), chlormequat (chlormequat chloride), choline chloride, cyclanilide, dikegulac, diflufenzopyr, dimethipin, ethephon, flumetralin, fluthiacet, forchlorfenuron, gibberellic acid, inabenfide, maleic hydrazide, mepiquat (mepiquat chloride), 1-methylcyclopropene (1-MCP), paclobutrazol, prohexadione (prohexadione calcium), prohydrojasmon, thidiazuron, triapenthenol, Tributyl phosphorotrithioate, trinexapac-ethyl and uniconazole.

Even more preferred inventive mixtures especially useful for seed treatment are those comprising compound II and compound IC having plant growth regulating activity selected from chlormequat (chlormequat chloride), choline chloride, cyclanilide, dimethipin, ethephon, forchlorfenuron, gibberellic acid, maleic hydrazide, mepiquat (mepiquat chloride), 1-methylcyclopropene (1-MCP), prohexadione (prohexadione calcium), pthidiazuron and trinexapac-ethyl.

More preferred inventive mixtures especially useful for foliar treatment are those comprising compound II and compound IC having plant growth regulating activity selected from 6-benzylaminopurine (=N-6-benzyladenine), chlormequat (chlormequat chloride), choline chloride, cyclanilide, dikegulac, diflufenzopyr, dimethipin, ethephon, flumetralin, fluthiacet, forchlorfenuron, gibberellic acid, inabenfide, maleic hydrazide, mepiquat (mepiquat chloride), 1-methylcyclopropene (1-MCP), paclobutrazol, prohexadione (prohexadione calcium), prohydrojasmon, thidiazuron, triapenthenol, Tributyl phosphorotrithioate, trinexapac-ethyl and uniconazole.

Even more preferred inventive mixtures especially useful for foliar treatment are those comprising compound II and compound IC having plant growth regulating activity selected from chlormequat (chlormequat chloride), choline chloride, cyclanilide, dimethipin, ethephon, forchlorfenuron, gibberellic acid, maleic hydrazide, mepiquat (mepiquat chloride), 1-methylcyclopropene (1-MCP), prohexadione (prohexadione calcium), pthidiazuron and trinexapac-ethyl.

Most preferred mixtures are those comprising compound II and compound IA displayed in Table 2A:

Beauveria bassiana strain PPRI 5339=A
IA=Compound IA II=Compound II

| No | IA | II |
|---|---|---|
| C-1. | azoxystrobin | A |
| C-2. | dimoxystrobin | A |
| C-3. | fluoxastrobin | A |
| C-4. | kresoxim-methyl | A |
| C-5. | orysastrobin | A |
| C-6. | picoxystrobin | A |
| C-7. | pyraclostrobin | A |
| C-8. | trifloxystrobin | A |
| C-9. | pyribencarb | A |
| C-10. | amisulbrom | A |
| C-11. | [(3S,6S,7R,8R)-8-beftnzyl-3-[(3-acetoxy-4-methoxy-pyridine-2-carbonyl)amino]-6-methyl-4,9-dioxo-1,5-dioxonan-7-yl] 2-methylpropanoate | A |
| C-12. | [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate | A |
| C-13. | [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate | A |
| C-14. | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate | A |
| C-15. | (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate | A |
| C-16. | bixafen | A |
| C-17. | boscalid | A |
| C-18. | fluopyram | A |
| C-19. | fluxapyroxad | A |
| C-20. | isopyrazam | A |
| C-21. | penflufen | A |
| C-22. | penthiopyrad | A |
| C-23. | sedaxane | A |
| C-24. | N-[9-(dichloromethylene)-1,2,3,4-tetrahydro-1,4-methanonaphthalen-5-yl]-3-(difluoromethyl)-1-methyl-1H-pyrazole-4-carboxamide | A |
| C-25. | 3-(difluoromethyl)-1-methyl-N-(1,1,3-trimethylindan-4-yl)pyrazole-4-carboxamide | A |
| C-26. | 3-(trifluoromethyl)-1-methyl-N-(1,1,3-trimethylindan-4-yl)pyrazole-4-carboxamide | A |
| C-27. | 1,3-dimethyl-N-(1,1,3-trimethylindan-4-yl)pyrazole-4-carboxamide | A |
| C-28. | 3-(trifluoromethyl)-1,5-dimethyl-N-(1,1,3-trimethylindan-4-yl)pyrazole-4-carboxamide | A |
| C-29. | 3-(difluoromethyl)-1,5-dimethyl-N-(1,1,3-trimethylindan-4-yl)pyrazole-4-carboxamide | A |
| C-30. | 1,3,5-trimethyl-N-(1,1,3-trimethylindan-4-yl)pyrazole-4-carboxamide | A |
| C-31. | (5,8-difluoroquinazolin-4-yl)-{2-[2-fluoro-4-(4-trifluoromethylpyridin-2-yloxy)-phenyl]-ethyl}-amine | A |
| C-32. | ametoctradin | A |
| C-33. | silthiofam | A |
| C-34. | difenoconazole | A |
| C-35. | epoxiconazole | A |
| C-36. | fluquinconazole | A |
| C-37. | ipconazole | A |
| C-38. | metconazole | A |
| C-39. | prothioconazole | A |
| C-40. | tebuconazole | A |
| C-41. | triticonazole, | A |
| C-42. | 1-[rel-(2S;3R)-3-(2-chlorophenyl)-2-(2,4-difluorophenyl)-oxiranylmethyl]-5-thiocyanato-1H-[1,2,4]triazole | A |
| C-43. | 2-[rel-(2S;3R)-3-(2-chlorophenyl)-2-(2,4-difluorophenyl)-oxiranylmethyl]-2H-[1,2,4]triazole-3-thiol | A |
| C-44. | prochloraz | A |
| C-45. | fenpropimorph | A |
| C-46. | metalaxyl | A |
| C-47. | carbendazim | A |
| C-48. | thiophanate-methyl | A |
| C-49. | metrafenone, | A |
| C-50. | pyrimethanil | A |
| C-51. | fludioxonil | A |
| C-52. | dimethomorph | A |
| C-53. | N-(1-(4-cyanophenyl)-ethanesulfonyl)-but-2-yl) carbamic acid-(4-fluorophenyl) ester | A |
| C-54. | mancozeb | A |
| C-55. | metiram | A |
| C-56. | dithianon | A |
| C-57. | 2,6-dimethyl-1H,5H-[1,4]dithiino[2,3-c:5,6-c']dipyrrole-1,3,5,7(2H,6H)-tetraone | A |
| C-58. | isotianil | A |
| C-59. | tiadinil | A |
| C-60. | prohexadione-calcium | A |
| C-61. | 4-cyclopropyl-N-(2,4-dimethoxyphenyl)thiadiazole-5-carboxamide | A |
| C-62. | 4,4-difluoro-3,3-dimethyl-1-(3-quinolyl)isoquinoline | A |
| C-63. | 2-butoxy-6-iodo-3-propylchromen-4-one | A |
| C-64. | N-(cyclopropylmethoxyimino-(6-difluoro-methoxy-2,3-difluoro-phenyl)-methyl)-2-phenyl acetamide | A |
| C-65. | 2-methoxy-acetic acid 6-tert-butyl-8-fluoro-2,3-dimethyl-quinolin-4-yl ester | A |
| C-66. | 3-[5-(4-methylphenyl)-2,3-dimethylisoxazolidin-3-yl]-pyridine | A |
| C-67. | 3-[5-(4-chloro-phenyl)-2,3-dimethylisoxazolidin-3-yl]-pyridine (pyrisoxazole) | A |
| C-68. | N-(6-methoxy-pyridin-3-yl) cyclopropane-carboxylic acid amide | A |
| C-69. | 5-chloro-1-(4,6-dimethoxy-pyrimidin-2-yl)-2-methyl-1H-benzoimidazole. | A |
| C-70. | carboxin | |
| C-71. | diniconazole | A |
| C-72. | diniconazole-M | A |
| C-73. | flutriafol | A |
| C-74. | tetraconazole | A |
| C-75. | triadimenol | A |
| C-76. | oxadixyl; | A |
| C-77. | hymexazole | A |
| C-78. | validamycin A | A |
| C-79. | fludioxonil | A |
| C-80. | probenfos | A |
| C-81. | quintozene | A |
| C-82. | tolclofos-methyl | A |
| C-83. | propamocarb | A |
| C-84. | propamo-carb-hydrochlorid | A |
| C-85. | validamycin | A |
| C-86. | fosetyl | A |
| C-87. | flusulfamide | A |
| C-88. | *Ampelomyces quisqualis* | A |
| C-89. | *Aspergillus flavus* | A |
| C-90. | *Aureobasidium pullulans* | A |
| C-91. | *Bacillus pumilus* | A |
| C-92. | *Bacillus pumilus* NRRL Accession No. B-30087 | A |
| C-93. | *Bacillus subtilis* | A |

-continued

| No | IA | II |
|---|---|---|
| C-94. | *Bacillus subtilis* NRRL-Nr. B-21661 | A |
| C-95. | *Bacillus subtilis* var. *amyloliquefaciens* FZB24 | A |
| C-96. | *Candida oleophila* I-82 | A |
| C-97. | *Candida saitoana* | A |
| C-98. | Chitosan | A |
| C-99. | *Clonostachys rosea* f. *catenulate* | A |
| C-100. | *Clonostachys rosea* f. *catenulate* isolate J1446 | A |
| C-101. | *Coniothyrium minitans* | A |
| C-102. | *Cryphonectria parasitica* | A |
| C-103. | *Endothia parasitica* | A |
| C-104. | *Cryptococcus albidus* | A |
| C-105. | *Fusarium oxysporum* | A |
| C-106. | FUSACLEAN® | A |
| C-107. | *Metschnikowia fructicola* | A |
| C-108. | *Microdochium dimerum* | A |
| C-109. | *Phlebiopsis gigantea* | A |
| C-110. | *Pseudozyma flocculosa* | A |
| C-111. | *Pythium oligandrum* DV74 | A |
| C-112. | *Reynoutria sachlinensis* | A |
| C-113. | *Talaromyces flavus* V117b | A |
| C-114. | *Trichoderma asperellum* SKT-1 | A |
| C-115. | *T. atroviride* LC52 | A |
| C-116. | *T. harzianum* T-22 | A |
| C-117. | *T. harzianum* TH 35 | A |
| C-118. | *T. harzianum* T-39 | A |
| C-119. | *T. harzianum* and *T. viride* | A |
| C-120. | *T. harzianum* ICC012 and *T. viride* ICC080 | A |
| C-121. | *T. polysporum* and *T. harzianum* | A |
| C-122. | *T. stromaticum* | A |
| C-123. | *T. virens* GL-21 | A |
| C-124. | *T. viride* | A |
| C-125. | *T. viride* TV1 | A |
| C-126. | *Ulocladium oudemansii* HRU3 | A |
| C-127. | flutolanil | A |

Table 2A-01

Equally most preferred mixtures are mixtures Q-1 to Q-127, comprising *Metarhizium anisopliae* FI-1045 as compound II instead of "A" and compound IA corresponding to C-1 to C-127 as defined in Table 2A.

Table 2A-02

Equally most preferred mixtures are mixtures R-1 to R-127, comprising *Metarhizium anisopliae* var. *acridum* strain IMI 330189 as compound II instead of "A" and compound IA corresponding to C-1 to C-127 as defined in Table 2A.

Table 2A-03

Equally most preferred mixtures are mixtures S-1 to S-127, comprising *Metarhizium anisopliae* var. *acridum* strain FI-985 as compound II instead of "A" and compound IA corresponding to C-1 to C-127 as defined in Table 2A.

Equally most preferred mixtures are those comprising compound II and compound IB displayed in Table 2B:

Beauveria bassiana strain PPRI 5339=A
IB=Comopund IB II=Compoound II

| No | IB | II |
|---|---|---|
| C'-1. | thiodicarb | A |
| C'-2. | ethiprole | A |
| C'-3. | fipronil | A |
| C'-4. | 4-[5-[3-chloro-5-(trifluoromethyl)phenyl]-5-(trifluoromethyl)-4H-isoxazol-3-yl]-N-[2-oxo-2-(2,2,2-trifluoroethylamino)ethyl]naphthalene-1-carboxamide | A |
| C'-5. | 4-[5-(3,5-dichlorophenyl)-5-(trifluoromethyl)-4H-isoxazol-3-yl]-2-methyl-N-[2-oxo-2-(2,2,2-trifluoroethylamino)ethyl]benzamide | A |
| C'-6. | lambda-cyhalothrin | A |
| C'-7. | alpha-cypermethrin | A |
| C'-8. | fenvalerate | A |
| C'-9. | permethrin | A |
| C'-10. | acteamiprid | A |
| C'-11. | chlothianidin | A |
| C'-12. | cycloxaprid | A |
| C'-13. | dinotefuran | A |
| C'-14. | flupyradifurone | A |
| C'-15. | imidacloprid | A |
| C'-16. | nitenpyram | A |
| C'-17. | sulfoxaflor | A |
| C'-18. | thiacloprid | A |
| C'-19. | thiamethoxam | A |
| C'-20. | 1-[(6-chloro-3-pyridyl)methyl]-7-methyl-8-nitro-5-propoxy-3,5,6,7-tetrahydro-2H-imidazo[1,2-a]pyridine | A |
| C'-21. | spinosad | A |
| C'-22. | abamectin | A |
| C'-23. | emamectin benzoate | A |
| C'-24. | 2-(5-fluoro-3-pyridyl)-5-(6-pyrimidin-2-yl-2-pyridyl)thiazole hydrofluoride | A |
| C'-25. | chlorfenapyr | A |
| C'-26. | flufenoxuron | A |
| C'-27. | teflubenzuron | A |
| C'-28. | metaflumizone | A |
| C'-29. | flubendiamide | A |
| C'-30. | chloranthraniliprole (rynaxypyr) | A |
| C'-31. | cyanthraniliprole (cyazypyr) | A |
| C'-32. | (R)-3-Chlor-N1-{2-methyl-4-[1,2,2,2-tetrafluor-1-(trifluormethyl)ethyl]phenyl}-N2-(1-methyl-2-methylsulsfonylethyl)phthalamid | A |
| C'-33. | (S)-3-Chlor-N1-{2-methyl-4-[1,2,2,2-tetrafluor-1-(trifluormethyl)ethyl]phenyl}-N2-(1-methyl-2-methyl-sulsulfonylethyl)phthalamid | A |
| C'-34. | 3-bromo-N-{2-bromo-4-chloro-6-[(1-cyclopropyl-ethyl)carbamoyl]phenyl}-1-(3-chlorpyridin-2-yl)-1H-pyrazole-5-carboxamide | A |
| C'-35. | methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate (known from WO 2007/043677) | A |
| C'-36. | N2-[2-(3-chloro-2-pyridyl)-5-[(5-methyltetrazol-2-yl)methyl]pyrazol-3-yl]-5-cyano-N1,3-dimethyl-phthalamide | A |
| C'-37. | 2-(5-ethylsulfinyl-2-fluoro-4-methylphenyl)-5-methyl-1,2,4-triazol-3-amine | A |
| C'-38. | 1-(5-ethylsulfinyl-2,4-dimethyl-phenyl)-3-methyl-1,2,4-triazole | A |
| C'-39. | afidopyropen | A |
| C'-40. | aldicarb | |
| C'-41. | benfuracarb | A |
| C'-42. | carbofuran | A |
| C'-43. | carbosulfan | A |
| C'-44. | oxamyl | A |
| C'-45. | pirimicarb | A |
| C'-46. | chlorfenvinphos | A |
| C'-47. | chlorpyrifos | A |
| C'-48. | chlorpyrifos-methyl | A |
| C'-49. | dichlorvos/DDVP | A |
| C'-50. | phorate | A |
| C'-51. | terbufos | A |
| C'-52. | bifenthrin | A |
| C'-53. | cypermethrin | A |
| C'-54. | zeta-cypermethrin | A |
| C'-55. | tefluthrin | A |
| C'-56. | flumetoquin | A |
| C'-57. | *Bacillus firmus* | A |
| C'-58. | *Bacillus firmus* of strain CNCM I-1582 | A |

Table 2A-01

Equally most preferred mixtures are mixtures T-1 to T-58, comprising *Metarhizium anisopliae* FI-1045 as compound II instead of "A" and compound IB corresponding to C'-1 to C'-58 as defined in Table 2B.

Table 1B-02

Equally most preferred mixtures are mixtures U-1 to U-58, comprising *Metarhizium anisopliae* var. *acridum* strain IMI 330189 as compound II instead of "A" and compound IB corresponding to C'-1 to C'-58 as defined in Table 2B.

Table 1B-03

Equally most preferred mixtures are mixtures V-1 to V-58, comprising *Metarhizium anisopliae* var *acridum* FI-985 as compound II instead of "A" and compound IB corresponding to C'-1 to C'-58 as defined in Table 2B.

In one most preferred embodiment the mixture comprises pyraclostrobin as compound IA and *Beauveria bassiana* strain PPRI 5339 as compound II.

In one most preferred embodiment the mixture comprises fluxapyroxad as compound IA and *Beauveria bassiana* strain PPRI 5339 as compound II.

In one most preferred embodiment the mixture comprises pyraclostrobin as compound IA and *Metarhizium anisopliae* FI-1045 as compound II.

In one most preferred embodiment the mixture comprises fluxapyroxad as compound IA and *Metarhizium anisopliae* FI-1045 as compound II.

In one most preferred embodiment the mixture comprises pyraclostrobin as compound IA and *Metarhizium anisopliae* var. *acridum* strain IMI 330189 as compound II.

In one most preferred embodiment the mixture comprises fluxapyroxad as compound IA and *Metarhizium anisopliae* var. *acridum* strain IMI 330189 as compound II.

In one most preferred embodiment the mixture comprises pyraclostrobin as compound IA and *Metarhizium anisopliae* var. *acridum* FI-985 as compound II.

In one most preferred embodiment the mixture comprises fluxapyroxad as compound IA and *Metarhizium anisopliae* var. *acridum* FI-985 as compound II.

In one most preferred embodiment the mixture comprises fipronil as compound IB and *Beauveria bassiana* strain PPRI 5339 as compound II.

In one most preferred embodiment the mixture comprises fipronil as compound IB and *Metarhizium anisopliae* FI-1045 as compound II.

In one most preferred embodiment the mixture comprises fipronil as compound IB and *Metarhizium anisopliae* var. *acridum* strain IMI 330189 as compound II.

In one most preferred embodiment the mixture comprises fipronil as compound IB and *Metarhizium anisopliae* var. *acridum* FI-985 as compound II.

The inventive mixtures can further contain one or more insecticides, fungicides, plant growth regulators and/or herbicides.

As stated above, the compounds of the inventive mixtures can be applied simultaneously, that is jointly or separately, or in succession.

The mixtures according to the present invention can be converted jointly with formulation auxiliaries into individual formulations (compositions) or can be converted jointly with formulation auxiliaries into customary formulations (co-formulation).

If applied separately or in succession, compound I and compound II are naturally be formulated separately.

Thus, in one embodiment, the compounds of the inventive mixtures can be present in a kit of parts comprising as part one formulated compound I as defined above; and as second component one formulated compound II as defined above.

According to one embodiment, individual components of the composition according to the invention such as parts of a kit or parts of a binary or ternary mixture may be mixed by the user himself in a spray tank or any other kind of vessel used for applications (e.g seed treater drums, seed pelleting machinery, knapsack sprayer) and further auxiliaries may be added, if appropriate. When living microorganisms, such as compound II, form part of such kit, it must be taken care that choice and amounts of the other parts of the kit (e.g. chemcial pesticidal agents) and of the further auxiliaries should not influence the viability of the microbial pesticides in the composition mixed by the user. Especially for bactericides and solvents, compatibility with the respective microbial pesticide has to be taken into account.

Consequently, one embodiment of the invention is a kit for preparing a usable pesticidal composition, the kit compring a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

The present invention therefore also relates to a kit of parts comprising as part one formulated compound I as defined above; and as second component one formulated compound II as defined above.

The kit of part may also optionally additionally comprise additional components III as outlined above, which can be also be provided separately packed, or, alternatively be present in combination with compound I or compound II, preferably with compound I.

The inventive mixtures can be converted individually or jointly into customary types of agrochemical compositions, e. g. solutions, suspensions, dusts, powders, pastes, granules, pressings, capsules, and mixtures thereof.

General examples for composition types for compound I and/or compound II are suspensions (e.g. SC, OD, FS), emulsifiable concentrates, capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Preferred examples of foliar formulation (or soil treatment) types for pre-mix compositions are GR: Granules
WP: wettable powders
WG: water dispersable granules (powders)
SG: water soluble granules
SL: soluble concentrates
ME: micro-emulsion
SC: aqueous suspension concentrate
CS: aqueous capsule suspension
OD: oil-based suspension concentrate, and SE: aqueous suspo-emulsion.

Preferred examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, antifoaming agents, colorants, stabilizers or nutrients, UV protectants, tackifiers and binders.

Especially for bactericides, choice and amounts of this auxiliary should not influence the viability of compound II (also if present in formulations comprising compound I).

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof. However, if such solvents are used, compatibility with compound II needs to be taken into account.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol.1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-subsituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-subsititued fatty acid amides are fatty acid glucamides or fatty acid alkanolamides. Examples of esters are fatty acid esters, glycerol esters or monoglycerides.

Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the inventive mixtures on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates. Suitable bactericides are bronopol and isothiazolinone derivatives such as alkylisothiazolinones and benzisothiazolinones.

Suitable anti-freezing agents are ethylene glycol, propylene glycol, urea and glycerin. Suitable anti-foaming agents are silicones, long chain alcohols, and salts of fatty acids. Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

When living microorganisms, such as compound II, form part of the compositions, such compositions can be prepared as compositions comprising besides the active ingredients at least one auxiliary (inert ingredient) by usual means (see e.g. H.D. Burges: Formulation of Micobial Biopesticides, Springer, 1998). Suitable customary types of such compositions are suspensions, dusts, powders, pastes, granules, pressings, capsules, and mixtures thereof. Examples for composition types are suspensions (e.g. SC, OD, FS), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). Herein, it has to be taken into account that each formulation type or choice of auxiliary should not influence the viability of the microorganism during storage of the composition and when finally applied to the plant propagation material. Suitable formulations are e.g. mentioned in WO 2008/002371, U.S. Pat. Nos. 6,955,912, 5,422,107.

Examples for suitable auxiliaries are those mentioned earlier herein, wherein it must be taken care that choice and amounts of such auxiliaries should not influence the viability of the microbial pesticides in the composition. Especially for bactericides and solvents, compatibility with the respective microorganism of the respective microbial pesticide has to be taken into account. In addition, compositions with microbial pesticides may further contain stabilizers or nutrients and UV protectants.

Suitable stabilizers or nutrients (H.D. Burges Formulaztion of Micobial Biopestcides) are e.g. alpha-tocopherol, trehalose, glutamate, potassium sorbate, various sugars like glucose, sucrose, lactose, maltodextrine.

Suitable UV protectants are e.g. inorganic compounds like titan dioxide, zinc oxide and iron oxide pigments or organic compounds like benzophenones, benzotriazoles, phenyltriazines.

The compositions may in addition to auxiliaries mentioned for compositions comprising compounds I herein optionally comprise 0.1-80% stabilizers or nutrients and 0.1-10% UV protectants.

General examples of suitable ratios for multiple formulation types referenced above are given in Agrow Reports DS243, T&F Informa, London, 2005.

Examples for composition types and their preparation are given below. It has to be noted that each compound present in the mixture of the present invention can be formulated separately and then, for preparation of the mixture, combined, e.g. in any spray device, or on the seed by consecutive or simultaneous application as outlined in more detail below.

CS formulations are particularly useful for compound I, less for compound II. In particular for compound II, granules, powders or suspensions (suspension concentrates) are preferred formulation type.

Herein, it has to be taken into account that each formulation type or choice of auxiliary should not influence the viability of the microorganism, if finally applied to the seed, soil by foliar application. As referenced above, a suitable formulation of compound II is referenced in WO 2008/002371.

i) Suspensions (SC, OD, FS)

In an agitated vessel 1-60 wt % of compound I or II or an inventive mixture are comminuted with addition of 2-10 wt % dispersants and wetting agents (e.g. sodium lignosulfonate and alcohol ethoxylate), 0.1-2 wt % thickener (e.g. xanthan gum) and up to 100 wt % water or an suitable oil to give a fine active substance suspension. Dilution with water gives a stable suspension of the active substance. For FS type composition up to 40 wt % binder (e.g. polyvinylalcohol) is added.

ii) Water-dispersible Granules and Water-soluble Granules (WG, SG)

1-80 wt % of compound I or II or an inventive mixture are are mixed to 100 wt % dispersants and wetting agents (e.g. sodium lignosulfonate and alcohol ethoxylate) and prepared as water-dispersible or water-soluble granules by means of technical appliances (e.g. extrusion, spraydrying, fluidized bed). Dilution with water gives a stable dispersion or solution of the active substance.

iii) Water-dispersible Powders and Water-soluble Powders (WP, WS)

1-80 wt % of a compound I or II or an inventive mixture are are mixed with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

iv) Gel (GW, GF)

In an mixer, 5-25 wt % of compound I or II or an inventive mixture are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.

v) Microcapsules (CS)

An oil phase comprising 5-50 wt % of a compound I, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4, 4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

vi) Dustable Powders (DP, DS)

1-10 wt % of compound I or II or an inventive mixture are mixed intimately with up to 100 wt % solid carrier, e.g. finely divided kaolin.

vii) Granules (GR, FG)

0.5-30 wt % of of compound I or II or an inventive mixture is mixed and associated with up to 100 wt % solid carrier (e.g. silicate). Granulation is achieved by extrusion, spray-drying or the fluidized bed.

The compositions types i) to vii) may optionally comprise further auxiliaries, such as 0.1-1 wt % bactericides, 5-15 wt % anti-freezing agents, 0.1-1 wt % anti-foaming agents, 0.1-80% stabilizers or nutrients, 0.1-10% UV protectants and 0.1-1 wt % colorants.

The seed treatment or soil treatment combinations and compositions comprising the inventive mixtures can also comprise or may be applied together and/or sequentially with further active compounds. These further useful active compounds can be fertilizers or micronutrient donors (such as Mo, Zn and/or Co).

The resulting agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Generally, a tank-mix formulation for foliar or soil application comprises 0.1 to 20 percent, especially 0.1 to 15 percent, of the desired ingredients, and 99.9 to 80 percent, especially 99.9 to 85 percent, of a solid or liquid auxiliaries (including, for example, a solvent such as water), where the auxiliaries can be a surfactant in an amount of 0 to 20 percent, especially 0.1 to 15 percent, based on the tank-mix formulation.

Typically, a pre-mix formulation for soil or for foliar application comprises 0.1 to 99.9 percent, especially 1 to 95 percent, of the desired ingredients, and 99.9 to 0.1 percent, especially 99 to 5 percent, of a solid or liquid adjuvant (including, for example, a solvent such as water), where the auxiliaries can be a surfactant in an amount of 0 to 50 percent, especially 0.5 to 40 percent, based on the pre-mix formulation.

Normally, a tank-mix formulation for seed treatment application comprises 0.25 to 80 percent, especially 1 to 75 percent, of the desired ingredients, and 99.75 to 20 percent, especially 99 to 25 percent, of a solid or liquid auxiliaries (including, for example, a solvent such as water), where the auxiliaries can be a surfactant in an amount of 0 to 40 percent, especially 0.5 to 30 percent, based on the tank-mix formulation.

Typically, a pre-mix formulation for seed treatment application comprises 0.5 to 99.9 percent, especially 1 to 95 percent, of the desired ingredients, and 99.5 to 0.1 percent, especially 99 to 5 percent, of a solid or liquid adjuvant (including, for example, a solvent such as water), where the auxiliaries can be a surfactant in an amount of 0 to 50 percent, especially 0.5 to 40 percent, based on the pre-mix formulation. Whereas commercial products will preferably be formulated as concentrates (e.g., pre-mix composition (formulation)), the end user will normally employ dilute formulations (e.g., tank mix composition).

The term "soil application" includes methods of applying to the soil can be via any suitable method, which ensures that the combination penetrates the soil, for example, nursery tray application, in furrow application, soil drenching, soil injection, drip irrigation, application through sprinklers or central pivot, incorporation into soil (broad cast or in band) are such methods.

Seed treatment methods for applying or treating inventive mixtures and compositions thereof to plant propagation material, especially seeds, are known in the art, and include dressing, coating, filmcoating, pelleting and soaking application methods of the propagation material. Such methods are also applicable to the combinations according to the invention. In a preferred embodiment, the inventive mixture is applied or treated on to the plant propagation material by a method such that the germination is not negatively impacted.

Accordingly, examples of suitable methods for applying (or treating) a plant propagation material, such as a seed, is seed dressing, seed coating or seed pelleting and alike.

It is preferred that the plant propagation material is a seed, seed piece (i.e. stalk) or seed bulb.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed either before or after the treatment.

Even distribution of the ingredients in inventive mixtures and adherence thereof to the seeds is desired during propagation material treatment. Treatment could vary from a thin film (dressing) of the formulation containing the combination, for example, a mixture of active ingredient(s), on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognizable.

An aspect of the present invention includes application of the inventive mixtures onto the plant propagation material in a targeted fashion, including positioning the ingredients in the combination onto the entire plant propagation material or on only parts thereof, including on only a single side or a portion of a single side. One of ordinary skill in the art would understand these application methods from the description provided in EP954213B 1 and WO06/112700.

The inventive mixtures can also be used in form of a "pill" or "pellet" or a suitable substrate and placing, or sowing, the treated pill, or substrate, next to a plant propagation material. Such techniques are known in the art, particularly in EP1124414, WO07/67042, and WO07/67044. Application of the combinations described herein onto plant propagation material also includes protecting the plant propagation material treated with the combination of the present invention by placing one or more pesticide-containing particles next to a pesticide-treated seed, wherein the amount of pesticide is such that the pesticide-treated seed and the pesticide-containing particles together contain an Effective Dose of the pesticide and the pesticide dose contained in the pesticide-treated seed is less than or equal to the Maximal Non-Phytotoxic Dose of the pesticide. Such techniques are known in the art, particularly in WO2005/120226.

Application of the combinations onto the seed also includes controlled release coatings on the seeds, wherein the ingredients of the combinations are incorporated into materials that release the ingredients over time. Examples of controlled release seed treatment technologies are generally known in the art and include polymer films, waxes, or other seed coatings, wherein the ingredients may be incorporated into the controlled release material or applied between layers of materials, or both.

Seed can be treated by applying thereto the compound s present in the inventive mixtures in any desired sequence or simultaneously.

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the active ingredient is applied to the soil but would include any application practice that would target the seed during the planting process.

Preferably, the treatment occurs before sowing of the seed so that the sown seed has been pre-treated with the combination. In particular, seed coating or seed pelleting are preferred in the treatment of the combinations according to the invention. As a result of the treatment, the ingredients in each combination are adhered on to the seed and therefore available for pest control.

The treated seeds can be stored, handled, sowed and tilled in the same manner as any other active ingredient treated seed.

For foliar application the inventive mixture is applied usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

In a further embodiment, either individual compounds of the inventive mixtures formulated as composition or partially premixed components, e. g. components set forth in the inventive mixtures may be mixed by the user in a spray tank and further auxiliaries and additives may be added, if appropriate (tank mix).

In a further embodiment, either individual components of the inventive mixture or partially premixed components, e.g. components comprising the compound I and II, can be applied jointly (e. g. after tankmix) or consecutively.

When applying compound IA, IB or IC and compound II sequentially, the time between both applications may vary e.g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day. Preferably, compound II is applied as last treatment.

The rates of application (use) of a combination vary, for example, according to type of use, type of crop, the compound (I) in the combination with I, type of plant propagation material (if appropriate), but is such that the active ingredients in the combination is an effective amount to provide the desired synergistically enhanced action (such as disease or pest control and plant heath effects) and can be determined by trials and routine experimentation known to one of ordinary skill in the art.

When employed in plant protection by foliar or soil spray application, the amounts of active substances applied are, depending on the kind of effect desired, from 0.001 to 2 kg per ha, preferably from 0.005 to 2 kg per ha, more preferably from 0.01 to 1.0 kg per ha, and in particular from 0.05 to 0.75 kg per ha.

In the case of compound II, the application rates preferably range from about $1 \times 10^6$ to $5 \times 10^{15}$ (or more) CFU/ha. Preferably, the spore concentration is about $1 \times 10^7$ to about $1 \times 10^{11}$ CFU/ha.

When employed in plant protection by seed treatment, the amount of the inventive mixtures is in the range from 0.01-10 kg, preferably from 0.1-1000 g, more preferably from 1-100 g per 100 kilogram of plant propagation material (preferably seeds).

In the case of compound II, the application rates with respect to plant propagation material (e.g. seed treatment) preferably range from about $1 \times 10^6$ to $1 \times 10^{12}$ (or more) CFU/seed. Preferably, the spore concentration is about $1 \times 10^6$ to about $1 \times 10^{11}$ CFU/seed. In the case of any microorganism, the application rates with respect to plant propagation material may also preferably range from about $1 \times 10^7$ to $1 \times 10^{14}$ (or more) CFU per 100 kg of seed, preferably from $1 \times 10^9$ to about $1 \times 10^{11}$ CFU per 100 kg of seed.

The methods according to the invention for controlling pests or increasing the health of plants of the abovementioned type is carried out in a manner known per se to those skilled in the art, depending on the intended aims and prevailing circumstances, that is to say by spraying, wetting, atomizing, dusting, brushing on, seed dressing, scattering or pouring of the composition.

Advantageously, the inventive mixtures are suitable for controlling the following fungal plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternate*), tomatoes (e.g. *A. solani* or *A. alternate*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes*: black dot), beans (e.g. *C. lindemuthianum*) and soybeans (e.g. *C. truncatum* or *C. gloeosporioides*); *Corticium* spp., e.g. *C. sasakii* (sheath blight) on rice; *Corynespora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*: Black Foot Disease) and ornamentals; *Dematophora* (teleomorph: *Rosellinia*) *necatrix* (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; *Esca* (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophilum* and/or *Botryosphaeria obtuse*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* on soybeans and *F. verticillioides* on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella cingulata* on vines, pome fruits and other plants and *G. gossypii* on cotton; Grain-staining complex on rice; *Guignardia bidwellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g.

*M. taxa*, *M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici*, Septoria blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsid*), soybeans (e.g. *P. megasperma*, syn. *P. sojae*), potatoes and tomatoes (e.g. *P. infestans*: late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or,rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collo-cygni* (Ramularia leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (Rhizoctonia spring blight) on wheat or barley; *Rhizopus stolonifer* (black mold, soft rot) on strawberries, carrots, cabbage, vines and tomatoes; *Rhynchosporium secalis* scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsii* or *S. sclerotiorum*); *Septoria* spp. on various plants, e.g. *S. glycines* (brown spot) on soybeans, *S. tritici* (Septoria blotch) on wheat and S. (syn. *Stagonospora*) *nodorum* (*Stagonospora blotch*) on cereals; *Uncinula* (syn. *Erysiphe*) *necator* (powdery mildew, anamorph: *Oidium tuckeri*) on vines; *Setospaeria* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (Stagonospora blotch, teleomorph: *Leptosphaeria* [syn. *eosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The mixtures according to the present inventino and compositions thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

The inventive mixtures exhibit also outstanding action against animal pests from the following orders:

Insects from the order of the lepidopterans (*Lepidoptera*), for example *Agrotis ypsilon*, *Agrotis segetum*, *Alabama argillacea*, *Anticarsia gemmatalis*, *Argyresthia conjugella*, *Autographa gamma*, *Bupalus piniarius*, *Cacoecia murinana*, *Capua reticulana*, *Cheimatobia brumata*, *Choristoneura fumiferana*, *Choristoneura occidentalis*, *Cirphis unipuncta*, *Cydia pomonella*, *Dendrolimus pini*, *Diaphania nitidalis*, *Diatraea grandiosella*, *Earias insulana*, *Elasmopalpus lignosellus*, *Eupoecilia ambiguella*, *Evetria bouliana*, *Feltia subterranea*, *Galleria mellonella*, *Grapholitha funebrana*, *Grapholitha molesta*, *Heliothis armigera*, *Heliothis virescens*, *Heliothis zea*, *Hellula undalis*, *Hibernia defoliaria*, *Hyphantria cunea*, *Hyponomeuta malinellus*, *Keiferia lycopersicella*, *Lambdina fiscellaria*, *Laphygma exigua*, *Leucoptera coffeella*, *Leucoptera scitella*, *Lithocolletis blancardella*, *Lobesia botrana*, *Loxostege sticticalis*, *Lymantria dispar*, *Lymantria monacha*, *Lyonetia clerkella*, *Malacosoma neustria*, *Mamestra brassicae*, *Orgyia*

*pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia* ni and *Zeiraphera canadensis,* beetles (*Coleoptera*), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicomis, Diabrotica semipunctata, Diabrotica* 12-*punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria,* flies, mosquitoes (*Diptera*), e.g. *Aedes aegypti, Aedes albopictus, Aedes vexans, Anastrepha ludens, Anopheles maculipennis, Anopheles crucians, Anopheles albimanus, Anopheles gambiae, Anopheles freebomi, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inomata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca domestica, Muscina stabulans, Oestrus ovis, Opomyza forum, Oscinella frit, Pegomya hysocyami, Phorbia antiqua, Phorbia brassicae, Phorbia coarctate, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* sp., *Simulium vittatum, Stomoxys calcitrans, Tabanus bovinus, Tabanus atratus, Tabanus lineola,* and *Tabanus similis, Tipula oleracea,* and *Tipula paludosa* thrips (*Thysanoptera*), e.g. *Dichromothrips corbetti, Dichromothrips* ssp, *Frankliniella fusca, Frankliniella occidentalis, Frankliniella tritici, Scirtothrips citri, Thrips oryzae, Thrips palmi* and *Thrips tabaci,* termites (*Isoptera*), e.g. *Calotermes flavicollis, Leucotermes flavipes, Heterotermes aureus, Reticulitermes flavipes, Reticulitermes virginicus, Reticulitermes lucifugus, Termes natalensis,* and *Coptotermes formosanus,* cockroaches (*Blattaria-Blattodea*), e.g. *Blattella germanica, Blattella asahinae, Periplaneta americana, Periplaneta japonica, Periplaneta brunnea, Periplaneta fuligginosa, Periplaneta australasiae,* and *Blatta orientalis,* true bugs (*Hemiptera*), e.g. *Acrostennum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla pini, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma* spp., and *Arilus critatus.* ants, bees, wasps, sawflies (*Hymenoptera*), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Monomorium pharaonis, Solenopsis geminata, Solenopsis invicta, Solenopsis richtefi, Solenopsis xyloni, Pogonomyrmex barbatus, Pogonomyrmex californicus, Pheidole megacephala, Dasymutilla occidentalis, Bombus* spp. *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile,* crickets, grasshoppers, locusts (*Orthoptera*), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis,*

*Kraussaria angulifera, Calliptamus italicus, Chortoicetes terminifera,* and *Locustana pardalina,*

Arachnoidea, such as arachnids (*Acarina*), e.g. of the families *Argasidae, Ixodidae* and *Sarcoptidae,* such as *Amblyomma americanum, Amblyomma variegatum, Ambryomma maculatum, Argas persicus, Boophilus annulatus, Boophilus decoloratus, Boophilus microplus, Dermacentor silvarum, Dermacentorandersoni, Dermacentor variabilis, Hyalomma truncatum, Ixodes ricinus, Ixodes rubicundus, Ixodes scapularis, Ixodes holocyclus, Ixodes pacificus, Orni-*

*thodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis;* Araneida, e.g. *Latrodectus mactans,* and *Loxosceles reclusa,* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* centipedes (Chilopoda), e.g. *Scutigera coleoptrata,* millipedes (Diplopoda), e.g. *Narceus* spp., earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus,* plant parasitic nematodes such as root-knot nematodes, *Meloidogyne arenaria, Meloidogyne chitwoodi, Meloidogyne exigua, Meloidogyne hapla, Meloidogyne incognita, Meloidogyne javanica* and other *Meloidogyne* species; cyst nematodes, *Globodera rostochiensis, Globodera pallida, Globodera tabacum* and other *Globodera* species, *Heterodera avenae, Heterodera glycines, Heterodera schachtii, Heterodera trifolii,* and other *Heterodera* species; seed gall nematodes, *Anguina funesta, Anguina tritici* and other *Anguina* species; stem and foliar nematodes, *Aphelenchoides besseyi, Aphelenchoides fragariae, Aphelenchoides ritzemabosi* and other *Aphelenchoides* species; sting nematodes, *Belonolaimus longicaudatus* and other *Belonolaimus* species; pine nematodes, *Bursaphelenchus xylophilus* and other *Bursaphelenchus* species; ring nematodes, *Criconema* species, *Criconemella* species, *Criconemoides* species, and *Mesocriconema* species; stem and bulb nematodes, *Ditylenchus destructor, Ditylenchus dipsaci, Ditylenchus myceliophagus* and other *Ditylenchus* species; awl nematodes, *Dolichodorus* species; spiral nematodes, *Helicotylenchus dihystera, Helicotylenchus multicinctus* and other *Helicotylenchus* species, *Rotylenchus robustus* and other *Rotylenchus* species; sheath nematodes, *Hemicycliophora* species and *Hemicriconemoides* species; *Hirshmanniella* species; lance nematodes, *Hoplolaimus columbus, Hoplolaimus galeatus* and other *Hoplolaimus* species; false root-knot nematodes, *Nacobbus aberrans* and other *Nacobbus* species; needle nematodes, *Longidorus elongates* and other *Longidorus* species; pin nematodes, *Paratylenchus* species; lesion nematodes, *Pratylenchus brachyurus, Pratylenchus coffeae, Pratylenchus curvitatus, Pratylenchus goodeyi, Pratylencus neglectus, Pratylenchus penetrans, Pratylenchus scribneri, Pratylenchus vulnus, Pratylenchus zeae* and other *Pratylenchus* species; *Radinaphelenchus cocophilus* and other *Radinaphelenchus* species; burrowing nematodes, *Radopholus similis* and other *Radopholus* species; reniform nematodes, *Rotylenchulus reniformis* and other *Rotylenchulus* species; *Scutellonema* species; stubby root nematodes, *Trichodorus primitivus* and other *Trichodorus* species; *Paratrichodorus minor* and other *Paratrichodorus* species; stunt nematodes, *Tylenchorhynchus claytoni, Tylenchorhynchus dubius* and other *Tylenchorhynchus* species and *Merlinius* species; citrus nematodes, *Tylenchulus semipenetrans* and other *Tylenchulus* species; dagger nematodes, *Xiphinema americanum, Xiphinema index, Xiphinema diversicaudatum* and other *Xiphinema* species; and other plant parasitic nematode species.

The term "plant" denotes various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as oilseed rape, canola, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn (maize), soybean, oilseed rape, canola, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e.g. conifers; and on the plant propagation material, such as seeds, and the crop material of these plants.

Preferred plants are OSR/canola, cereals, rice, legumes/pulses, alfalfa, sugarbeet, mustard, sorghum, ornamentals, tobacco, corn, soybean, sugarcane, sunflower, potato, cotton, fruits (temperate and tropical), grapes and vegetables.

More preferred plants are corn, soybean, sugarcane, sunflower, potato, cotton, fruits (temperate and tropical), grapes, vegetables and coffee.

Most preferred plants are fruits (temperate and tropical), grapes, vegetables, coffee.

The term "plants" is also to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties. Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibittors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i.e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e.g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or ExpressSun® sunflowers (DuPont, USA) being tolerant to sulfonyl ureas, e.g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus Bacillus, particularly from Bacillus thuringiensis, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. Photorhabdus spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against Phytophthora infestans derived from the mexican wild potato Solanum bulbocastanum) or T4-lysozym (e.g. potato cultivars capable of synthesizing these proteins with increased resistance against bacteria such as Erwinia amylvora). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

In the mixtures and compositions, the compound ratios are advantageously chosen so as to produce a synergistic effect.

The term "synergstic effect" is understood to refer in particular to that defined by Colby's formula (Colby, S. R., "Calculating synergistic and antagonistic responses of herbicide combinations", Weeds, 15, pp. 20-22, 1967).

The term "synergistic effect" is also understood to refer to that defined by application of the Tammes method, (Tammes, P. M. L., "Isoboles, a graphic representation of synergism in pesticides", Netherl. J. Plant Pathol. 70, 1964).

According to the invention, the solid material (dry matter) of the microorganisms such as compound II or antifungal biocontrol agents (with the exception of oils) are considered as active components (e.g. to be obtained after drying or evaporation of the extraction medium or the suspension medium in case of liquid formulations of the microbial pesticides).

The total weight ratios of compositions comprising at least one microbial pesticide in the form of viable microbial cells including dormant forms, can be determined using the amount of CFU of the respective microorganism to calclulate the total weight of the respective active component with the following equation that $1\times10^9$ CFU equals one gram of total weight of the respective active component. Colony forming unit is measure of viable microbial cells, in particular fungal and bacterial cells. In addition, here "CFU" may also be understood as the number of (juvenile) individual nematodes in case of (entomopathogenic) nematode biopesticides, such as Steinernema feltiae. In the binary mixtures and compositions according to the invention the weight ratio of the component 1) and the component 2) generally depends from the properties of the active components used, usually it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to a further embodiments of the binary mixtures and compositions, the weight ratio of the component 1) and the component 2) usually is in the range of from 1000:1 to 1:1, often in the range of from 100: 1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to a further embodiments of the binary mixtures and compositions, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

In the ternary mixtures, i.e. compositions according to the invention comprising the component 1) and component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component 1).

These ratios are also suitable for inventive mixtures applied by seed treatment.

The fungicidal action of the mixtures according to the invention can be shown by the tests described below.

A) Microtiter Plate Tests

The chemical pesticides (e.g. compounds IA, IB or IC) were formulated separately as a stock solution having a concentration of 10000 ppm in dimethyl sulfoxide. The stock solutions of the chemical pesticides were mixed according to the ratio, diluted to the stated concentrations and pipetted onto a filter micro titer plate (MTP). A spore suspension of the pathogen (e.g. *Botrytis cinerea*, *Septoria tritici*, etc.) in e.g. aqueous biomalt solution was added as well as different concentrations of spores or cells of the microbial pesticide (e.g. compound II). The plates were incubated at optimal temperature depending on the pathogen and further processed 1-7 days after incubation. The supernatant was removed using CaptiVac Vacuum Collar and a vacuum filter pump. The remaining cell pellet was resolved in water and DNA was extracted. The growth of the pathogen was quantified via quantitative Real Time PCR using species- or strain-specific primers. To assess synergistic effects growth of the fungal pathogens was calculated in comparison to the different controls containing either the chemical pesticide or the microbial pesticide alone.

The measured parameters were compared to the growth of the active compound-free control variant (100%) and the fungus-free and active compound-free blank value to determine the relative growth in % of the pathogens in the respective active compounds.

The expected efficacies of active compound combinations were determined using Colby's formula (Colby, S. R., Calculating synergistic and antagonistic responses of herbicide combinations, Weeds, 15, pp. 20-22, 1967) and compared with the observed efficacies.

$$E = x+y-x \cdot y/100 \qquad \text{Colby's formula:}$$

E expected efficacy, expressed in % of the untreated control, when using the mixture of the active compounds A (e.g. compound IA, IB or IC) and B (e.g. compound II) at the concentrations a and b x efficacy, expressed in % of the untreated control, when using the active compound A at the concentration a y efficacy, expressed in % of the untreated control, when using the active compound B at the concentration b.

USE EXAMPLE FM-1

Activity Against *Septoria tritici*, the Causal Agent of Leaf Blotch on Wheat

A spore suspension of *Septoria tritici* in an aqueous biomalt solution was used. The plates were placed in a water vapor-saturated chamber at a temperature of 18° C.

B) Greenhouse Tests

The chemical pesticides (e.g. compounds IA, IB or IC) were formulated separately or together as a stock solution comprising 25 mg of active substance which was made up to 10 ml using a mixture of acetone and/or dimethyl sulfoxide (DMSO) and the emulsifier Wettol EM 31 (wetting agent having emulsifying and dispersing action based on ethoxylated alkylphenols) in a volume ratio of solvent/emulsifier of 99 to 1. This solution was then made up to 100 ml using water. This stock solution was diluted with the solvent/emulsifier/water mixture described to the active substance concentration given below. The microbial pesticide (e.g. compound II) was cultivated as described herein and was diluted with water to the concentration given below.

USE EXAMPLE FG-1

Activity Against Early Blight on Tomatoes Caused by *Phytophthora Infestans* with Protective Application Young seedlings of tomato plants were grown in pots. The plants were sprayed to runoff with an aqueous suspension containing the concentration of chemical pesticide stated below. Simultaneously or up to 6 hours later, the plants were sprayed with an aquous suspension containg the concentration of the microbial pesticide stated below. The next day, the treated plants were inoculated with an aqueous suspension of sporangia of Phytophthora infestans. After inoculation, the trial plants were immediately transferred to a humid chamber. After 6 days at 18 to 20° C. and a relative humidity close to 100%, the extent of fungal attack on the leaves was visually assessed as % diseased leaf area.

USE EXAMPLE FG-2

Curative Action Against *Puccinia Recondita* on Wheat (Brown Rust of Wheat)

Leaves of potted wheat seedlings of the cultivar "Kanzler" were dusted with a suspension of spores of brown rust of wheat (*Puccinia recondita*). The plants were then placed in a chamber with high atmospheric humidity (90 to 95%), at 20-22° C., for 24 hours.

During this time, the spores germinated and the germinal tubes penetrated into the leaf tissue. The next day, the infected plants were sprayed to runoff point with an aqueous suspension having the concentration of chemical pesticide stated below. Simultaneously or up to 6 hours later, the plants were sprayed with an aquous suspension containg the concentration of microbial pesticide stated below. After drying of the sprayed suspension, the test plants were returned into the greenhouse and cultivated at temperatures between 20 and 22° C. and at 65 to 70% relative atmospheric humidity for a further 7 days. The extent of the rust development on the leaves was then determined visually.

USE EXAMPLE FG-3

Protective Action Against *Puccinia Recondita* on Wheat (Brown Rust of Wheat)

Leaves of potted wheat seedlings of the cultivar "Kanzler" were sprayed to runoff point with an aqueous suspension having the concentration of chemical pesticide stated below. Simultaneously or up to 6 hours later, the plants were sprayed with an aquous suspension containg the concentration of microbial pesticide stated below. The next day, the treated plants were dusted with a suspension of spores of brown rust of wheat (*Puccinia recondite*). The plants were then placed in a chamber with high atmospheric humidity (90 to 95%), at 20-22° C., for 24 hours. During this time, the spores germinated and the germinal tubes penetrated into the leaf tissue. The next day, the test plants were returned into the greenhouse and cultivated at temperatures between 20 and 22° C. and at 65 to 70% relative atmospheric humidity for a further 7 days. The extent of the rust development on the leaves was then determined visually.

USE EXAMPLE FG-4

Protective Action Against *Blumeria Graminis Tritici* on Wheat (Mildew of Wheat)

Leaves of potted wheat seedlings of the cultivar "Kanzler" were sprayed to runoff point with an aqueous suspension having the concentration of chemical persticide stated below. Simultaneously or up to 6 hours later, the plants were sprayed with an aquous suspension containg the concentration of microbial pesticide stated below. The next day, the treated plants were dusted with a suspension of spores of mildew of wheat (*Blumeria graminis tritici*). The plants were then returned into the greenhouse and cultivated at temperatures between 20 and 24° C. and at 60 to 90% relative atmospheric humidity for a further 7 days. The extent of the mildew development on the leaves was then determined visually.

USE EXAMPLE FG-5

Protective Action Against *Sphaerotheca Fuliginea* on Cucumber (Mildew of Cucumber)

Leaves of potted cucumber seedlings (in the germ layer stage) were sprayed to runoff point with an aqueous suspension having the concentration of chemical pesticide stated below. Simultaneously or up to 6 hours later, the plants were sprayed with an aquous suspension containg the concentration of microbial pesticide stated below. The next day, the treated plants were dusted with a suspension of spores of mildew of cucumber (*Sphaerotheca fuliginea*). The plants were then returned into the greenhouse and cultivated at temperatures between 20 and 24° C. and at 60 to 80% relative atmospheric humidity for a further 7 days. The extent of the mildew development on the seed leaves was then determined visually.

The insecticidal action of the mixtures according to the invention can be shown by the tests as described below using the respective microbial pesticide (e.g. compound II) as formulated product or conidia/spores suspensions in sterile water with 0.05% v/v adjuvant (e.g. Tween® 80).

I. Compatibility of Chemical Pesticides (e.g. Compound IA, IB or IC) with Microbial Pesticides (e.g. Compound II)
Materials:
autoclaved medium adapted to the microbial pesticide to cultivate: potato dextrose agar medium (PDA), malt dextrose agar (MEA), potato carrot agar (PCA) or sabouraud dextrose agar (SDA)
sterile plates (e.g. Petri dishes), vessels (e.g. bottles) and sterile water.
For dilution of oil formulations it may be recommended to use kerosene or add Tween® 80 at 0.05% v/v to the sterile water.

A) Liquid Mixture in a Bottle

Chemical pesticide formulations are prepared from stock solutions (see above) in sterile water or water with 0.05% v/v Tween® 80 using a logarithmic range of concentrations expressed in ppm. The spore/conidia solution of the microbial pesticide at the concentration stated below is pipetted into each vessel containing the chemical pesticide. The vessels are shaken to ensure the complete suspension of the microbial pesticide and kept at room temperature (24-26° C.) during the experiment.

The mixture is then diluted to a concentration of $1 \times 10^6$ spores/conidia per ml. A fixed volume (i.e. 1 mL) of each treatment is pipetted at different time intervals and distributed aseptically onto a plate containing the autoclaved medium for culture.

B) Solid Plate Assay

Chemical pesticide at various test concentrations is added to a series of vessels containing warm autoclaved medium before it gets solid, and then poured into separate pates using 4 replicates per treatment. After the medium solidified, the spore/conidia solution (i.e. $1\times10^6$ spores/conidia per mL) is pipetted into each plate.

In both methods, 4 replicates are used and the plates are cultured at 28° C. and 80% rel. humidity for 24 to 48 h. Compatibility is determined after 1, 24 h and optionally 48 h as follows: 1) by counting germinated vs. non-germinated spores/conidia (counted≥100) in the mixture using a microscope and hemacytometer to establish the germination rate in %, or number of germinated spores/conidia; or 2) by determining colony diameter in mm, speed of growth in mm/day, shape of the colony and/or color of the colony on the plates. All parameters are compared to a suspension of spores/conidia in absence of chemical pesticide (negative control).

II. Determination of Sub-lethal Rates of the Chemical Pesticide (e.g. Compound IA, IB or IC) and Microbial Pesticide (e.g. compound II)

These studies can be conducted in the growth chamber, greenhouse and/or in the field. Test plants are either dipped or sprayed with spore/conidia suspensions of the microbial pesticide at various concentrations or with formulations of the chemical pesticide at various concentrations and subsequently left to dry. Then, the plants are artificially or naturally infested with the respective target insect species. Assessments are carried out at different timings after treatment. The parameters evaluated are: efficacy (counting dead insects vs. alive), feeding damage, and/or plant vigor. All parameters are determined in comparison to the untreated insect-infested plants (free of microbialpesticide and chemical pesticide, respectively).

III. Synergism Trials

A synergism trial will contain at least the following treatments:

a) chemical pesticide at the sub-lethal rate a b) microbial pesticide alone at the sub-lethal rate b c) mixture of the chemical pesticide at rate a and the microbial pesticide at rate b d) Untreated control.

The microbial pesticide suspensions and chemical pesticide formulations can be prepared as described above. The expected efficacies of the mixtures are determined using Colby's formula as described above and compared with the observed efficacies. Efficacy is determined as insect mortality (number of dead insects vs. number of insects tested in the experiment) and/or % feeding damage.

USE EXAMPLE 1-1

Curative Action Against Stink Bugs (*Nezara viridula*) in the Field

Soybean plants are grown in the field allowing natural infestation with stinkbugs. Plants were sprayed with the respective treatments. Efficacy was determined at 3, 7 and 14 days after treatment.

USE EXAMPLE 1-2

Curative Action Against Whiteflies (*Bemisia tabaci*) in the Field

Tomato plants were grown in the field allowing natural infestation with whiteflies. Plants were sprayed with the respective treatments. Efficacy on adults was determined at 3, 7, 14 and 21 days after treatment, on larvae at 21 days after treatment.

USE EXAMPLE 1-3

Protective Action Against Thrips (*Frankiniella occidentalis*) in the Growth Chamber Lima bean plants were grown in small pots. Plants were dipped into the respective treatments. Plants were put into plastic cups and left to dry. Once dried, plants were infested with 15 adult thrips and cups were closed. Efficacy was evaluated at 3, 7 and 10 days after treatment.

USE EXAMPLE I-4

Protective Action Against Southern Armyworm (*Spodoptera eridiana*)

Lima bean leaves were cut and dipped into the respective treatments and placed in Petri dishes on wet filter paper to keep humidity. Once the surface of the leaves dried, 5 first/second instar larvae were infested per petri dish. Efficacy was evaluated at 3, 7 and 10 days after treatment.

USE EXAMPLE 5

Protective Action Against Colorado Potato Beetle (*Leptinotarsa decemlineata*) in the Field Potato plants were grown in the field allowing natural infestation with Colorado potato beetles. Plants were sprayed with the respective treatments. Efficacy was determined at 3, 7 and 14 days after treatment.

The plant health improving action of the mixtures according to the invention can be shown by the tests described below.

USE EXAMPLE H-1

Action Against Drought Stress

Drought stress tolerance can be tested e.g. on duckweed plants grown in 24-well microplates according to the method disclosed J. Plant Growth Regul. 30, 504-511 (2011).

The measured parameters were compared to the growth of the active compound-free control variant under drought stress (e.g. PEG treatment) (0%) and the active compound-free blank value without drought stress (e.g. PEG-fee) (100%) to determine the relative growth in % in the respective active compounds. The expected efficacies of active compound combinations were determined using Colby's formula as described above.

The invention claimed is:
1. Synergistic mixtures comprising, as active components,
1) one insecticidal compound IB selected from the group consisting of:
M-3 sodium channel modulators from the class of pyrethroids: cyfluthrin, and beta-cyfluthrin;

M-23 Mitochondrial complex II electron transport inhibitors: cyflumetofen;
M-24 Ryanodine receptor-modulators from the class of diamides: cyantraniliprole (cyazypyr);
M-25 Others: afidopyropen;

and 2) one compound II, wherein compound II is Beauveria bassiana PPRI 5339 and wherein the ratio by weight of compound IB to compound II is from 1:1 to 1:1000 and compound II is prepared with at least $10^6$ CFU/g.

2. The mixture according to claim 1 comprising as compound IB one insecticidal compound, wherein the compound is cyantraniliprole (cyazypyr).

3. A pesticidal composition, comprising a liquid or solid carrier and a mixture as defined in claim 1.

4. A method for controlling pests and/or improving the health of plants, wherein the pest, their habitat, breeding grounds, their locus or the plants to be protected against pest attack are treated with an effective amount of a mixture as defined in claim 1.

5. A method for protection of plant propagation material from pests and/or improving the health of plants grown from said plant propagation material, wherein the plant propagation material are treated with an effective amount of a mixture as defined in claim 1.

6. A method for protection of plant propagation material from pests and/or improving the health of plants grown from said plant propagation material, wherein the soil, wherein seeds are sown, is treated with an effective amount of a mixture as defined in claim 1.

7. Plant propagation material, comprising the mixture as defined in claim 1 in an amount of from 0.01 g to 10 kg per 100 kg of plant propagation material.

* * * * *